(12) United States Patent
Ali et al.

(10) Patent No.: US 8,354,394 B2
(45) Date of Patent: Jan. 15, 2013

(54) DIURETICS

(75) Inventors: Amjad Ali, Freehold, NJ (US);
Christopher Franklin, Quincy, MA (US); Ravi Nargund, East Brunswick, NJ (US); Michael Man-Chu Lo, Edison, NJ (US); Lin Yan, East Brunswick, NJ (US); Pei Huo, Millburn, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/504,581

(22) PCT Filed: Oct. 22, 2010

(86) PCT No.: PCT/US2010/053680
§ 371 (c)(1),
(2), (4) Date: Apr. 27, 2012

(87) PCT Pub. No.: WO2011/053519
PCT Pub. Date: May 5, 2011

(65) Prior Publication Data
US 2012/0208838 A1 Aug. 16, 2012

Related U.S. Application Data

(60) Provisional application No. 61/256,069, filed on Oct. 29, 2009.

(51) Int. Cl.
*A61K 31/655* (2006.01)
*C07D 491/06* (2006.01)
*A61P 9/12* (2006.01)

(52) U.S. Cl. ......... 514/149; 514/869; 534/551; 534/556

(58) Field of Classification Search .................. None
See application file for complete search history.

(56) References Cited

U.S. PATENT DOCUMENTS

| | | |
|---|---|---|
| 4,383,998 A | 5/1983 | Esanu |
| 4,923,970 A | 5/1990 | Michejda et al. |
| 5,130,252 A | 7/1992 | Eck et al. |
| 2008/0312241 A1 | 12/2008 | Cornett et al. |

*Primary Examiner* — Fiona T Powers
(74) *Attorney, Agent, or Firm* — Richard S. Parr; Catherine D. Fitch

(57) ABSTRACT

A compound having the structure (I) wherein R is selected from the group consisting of 1) and 2), or a pharmaceutically acceptable salt thereof, and methods of using the compounds for treating hypertension.

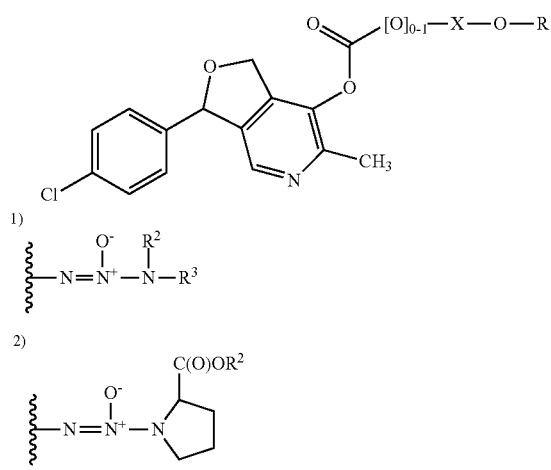

9 Claims, No Drawings

DIURETICS

BACKGROUND OF THE INVENTION

US 2005/0059655 describes nitrosated and nitrosylated furosemide derivatives (examples 1-16) having one or two nitroxy groups attached. The compounds are described as useful for treating conditions resulting from excessive water retention, cardiovascular disease, diabetes, oxidative stress, endothelial dysfunction, cirrhosis, pre-eclampsia, osteoporosis, and nephropathy.

U.S. Pat. No. 4,383,998 generically claims cicletanine. U.S. Pat. No. 5,026,855 claims the (+) enantiomer of cicletanine and compositions comprising the (+) enantiomer, and methods of preparation.

SUMMARY OF THE INVENTION

The present invention includes nitric oxide linked cicletanine, and derivatives thereof, including various pharmaceutically acceptable salts and hydrates of these forms, and pharmaceutical formulations for controlled and sustained delivery of these forms to a patient. The salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention also includes a method for treating hypertension, pulmonary arterial hypertension (PAH), congestive heart failure, conditions resulting from excessive water retention, cardiovascular disease, diabetes, oxidative stress, endothelial dysfunction, cirrhosis, pre-eclampsia, osteoporosis or nephropathy, comprising administering a compounds of the invention to a patient having such a condition, or being at risk to having such condition.

DETAILED DESCRIPTION OF THE INVENTION AND PREFERRED EMBODIMENTS

Compounds of the invention have the general formula I:

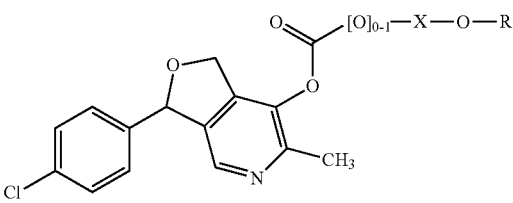

or a stereoisomer thereof, or a pharmaceutically acceptable salt thereof, or a pharmaceutically acceptable salt of the stereoisomer thereof, wherein
R is selected from the group consisting of 1)
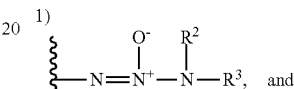
and 2)
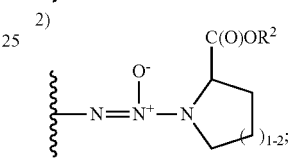

$R^2$, in each instance in which it occurs, is independently —$C_{1-6}$alkyl;
$R^3$ is —$C_{1-6}$alkyl or —$C_{1-6}$alkylene-aryl
X' is selected from the group consisting of 1)
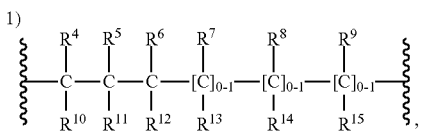

2)
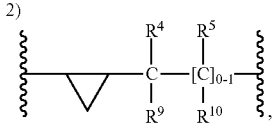

3)
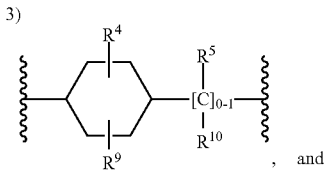
, and

4)
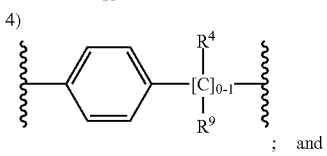
; and $R^4$, $R^5$, $R^6$, $R^7$, $R^8$, $R^9$, $R^{10}$, $R^{11}$, $R^{12}$, $R^{13}$, $R^{14}$ and $R^{15}$ are independently selected from the group consisting of hydrogen, $C_{1-6}$ alkyl, halogen, and —O—$C_{1-6}$ alkyl.

In one embodiment of the invention, X is selected from the group consisting of
—$CH_2CH_2CH_2CH_2$—,
—$CH_2CH(CH_3)CH_2CH_2$—,
—$CH(CH_3)CH_2CH_2CH_2$—, —CH₂CH₂CH(CH₃)CH₂—,
—CH₂CH₂CH₂CH(CH₃)—,
—CH(CH₃)CH₂CH₂—,
—CH₂CH₂CH₂CH₂CH₂—,
—CH₂CH₂CH(CH₃)CH₂CH₂—
—CH(CH₃)CH₂CH₂CH₂CH₂—

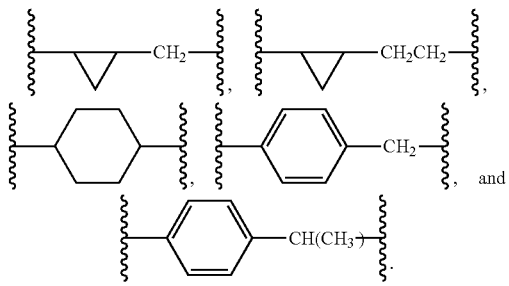

In another embodiment of the invention, R² is selected from the group consisting of —CH₃, —CH₂CH₃, —C(CH₃)₃, and —CH(CH₃)₂.

In another embodiment of the invention, R³ is selected from the group consisting of —CH₃, —CH₂CH₃, —C(CH₃)₃, —CH(CH₃)₂ and —CH₂—C₆H₅.

In another embodiment of the invention, the compound is selected from the group consisting of (3S)-3-(4-Chlorophenyl)-6-methyl-1,3-dihydrofuro[3,4-c]pyridin-7-yl 4-[({[(1Z)-2-tert-butyl-2-methyl-1-oxido-1λ⁵-diazan-1-ylidene]amino}oxy)methyl]benzoate, (3S)-3-(4-Chlorophenyl)-6-methyl-1,3-dihydrofuro[3,4-c]pyridin-7-yl 4-[1-({[(1Z)-2-tert-butyl-2-methyl-1-oxido-1λ⁵-diazan-1-ylidene]amino}oxy)ethyl]benzoate, (3S)-3-(4-Chlorophenyl)-6-methyl-1,3-dihydrofuro[3,4-c]pyridin-7-yl 4-[({[(1Z)-2,2-diethyl-1-oxide-1λ⁵-diazan-1-ylidene]amino}oxy)methyl]benzoate, (3S)-3-(4-Chlorophenyl)-6-methyl-1,3-dihydrofuro[3,4-c]pyridin-7-yl 4-({[(1Z)-2-tert-butyl-2-methyl-1-oxide-1λ⁵-diazan-1-ylidene]amino}oxy)cyclohexanecarboxylate, (3S)-3-(4-Chlorophenyl)-6-methyl-1,3-dihydrofuro[3,4-c]pyridin-7-yl cis-4-({[(1Z)-2-tert-butyl-2-methyl-1-oxidohydrazono]amino}oxy)cyclohexanecarboxylate, (3S)-3-(4-Chlorophenyl)-6-methyl-1,3-dihydrofuro[3,4-c]pyridin-7-yl trans-4-{[(1Z)-2-tert-butyl-2-methyl-1-oxidohydrazono]amino}oxy)cyclohexanecarboxylate, (3S)-3-(4-Chlorophenyl)-6-methyl-1,3-dihydrofuro[3,4-c]pyridin-7-yl trans-4-({[(1Z)-2,2-diethyl-1-oxide-1λ⁵-diazan-1-ylidene]amino}oxy)cyclohexanecarboxylate, (3S)-3-(4-Chlorophenyl)-6-methyl-1,3-dihydrofuro[3,4-c]pyridin-7-yl 5-({[(1Z)-2-tert-butyl-2-methyl-1-oxide-1λ⁵-diazan-1-ylidene]amino}oxy)pentanoate, (3S)-3-(4-Chlorophenyl)-6-methyl-1,3-dihydrofuro[3,4-c]pyridin-7-yl 5-({[(1Z)-2-tert-butyl-2-methyl-1-oxido-1λ⁵-diazan-1-ylidene]amino}oxy)-3-methylpentanoate, (3S)-3-(4-Chlorophenyl)-6-methyl-1,3-dihydrofuro[3,4-c]pyridin-7-yl (3R)-5-({[(1Z)-2-tert-butyl-2-methyl-1-oxido-1λ⁵-diazan-1-ylidene]amino}oxy)-3-methylpentanoate, (3S)-3-(4-Chlorophenyl)-6-methyl-1,3-dihydrofuro[3,4-c]pyridin-7-yl (3,5)-5-({[(1Z)-2-tert-butyl-2-methyl-1-oxido-1λ⁵-diazan-1-ylidene]amino}oxy)-3-methylpentanoate, (3S)-3-(4-Chlorophenyl)-6-methyl-1,3-dihydrofuro[3,4-c]pyridin-7-yl 5-({[(1Z)-2-tert-butyl-2-methyl-1-oxido-1λ⁵-diazan-1-ylidene]amino}oxy)-2-methylpentanoate, (3S)-3-(4-Chlorophenyl)-6-methyl-1,3-dihydrofuro[3,4-c]pyridin-7-yl 5-({[(1Z)-2-tert-butyl-2-methyl-1-oxide-1λ⁵-diazan-1-ylidene]amino}oxy)-4-methylpentanoate, (3S)-3-(4-Chlorophenyl)-6-methyl-1,3-dihydrofuro[3,4-c]pyridin-7-yl 5-([({1Z)-2-tert-butyl-2-methyl-1-oxido-1λ⁵-diazan-1-ylidene]amino}oxy)hexanoate, (3S)-3-(4-Chlorophenyl)-6-methyl-1,3-dihydrofuro[3,4-c]pyridin-7-yl 4-({[(1E)-2-tert-butyl-2-methyl-1-oxidohydrazono]amino}oxy)-2-methylbutanoate, (3S)-3-(4-Chlorophenyl)-6-methyl-1,3-dihydrofuro[3,4-c]pyridin-7-yl 2-[2-({[(1Z)-2-tert-butyl-2-methyl-1-oxidohydrazono]amino}oxy)ethyl]-trans-cyclopropanecarboxylate, (3S)-3-(4-Chlorophenyl)-6-methyl-1,3-dihydrofuro[3,4-c]pyridin-7-yl 2-[2-({[(1Z)-2-tert-butyl-2-methyl-1-oxidohydrazono]amino}oxy)ethyl]-cis-cyclopropanecarboxylate, (3S)-3-(4-Chlorophenyl)-6-methyl-1,3-dihydrofuro[3,4-c]pyridin-7-yl 2-[({[2-tert-butyl-2-methyl-1-oxido-1λ⁵-diazan-1-ylidene]amino}oxy)methyl]cyclopropanecarboxylate, Ethyl 1-{(Z)-[(5-{[(3S)-3-(4-chlorophenyl)-6-methyl-1,3-dihydrofuro[3,4-c]pyridin-7-yl]oxy}-5-oxopentyl)oxy]-NNO-azoxy}-L-prolinate, (3S)-3-(4-Chlorophenyl)-6-methyl-1,3-dihydrofuro[3,4-c]pyridin-7-yl-5-({[(1Z)-2-benzyl-2-isopropyl-1-oxido-1λ⁵-diazan-1-ylidene]amino}oxy)pentanoate, 5-({[(1Z)-2-tert-butyl-2-methyl-1-oxido-1λ⁵-diazan-1-ylidene]amino}oxy)pentyl (3S)-3-(4-chlorophenyl)-6-methyl-1,3-dihydrofuro[3,4-c]pyridin-7-yl carbonate, 5-({[(1Z)-2-tert-butyl-2-methyl-1-oxido-1λ⁵-diazan-1-ylidene]amino}oxy)-3-methylpentyl (3S)-3-(4-chlorophenyl)-6-methyl-1,3-dihydrofuro[3,4-c]pyridin-7-yl carbonate, (2S)-6-([{(1Z)-2-tert-butyl-2-methyl-1-oxido-1λ⁵-diazan-1-ylidene]amino}oxy)hexan-2-yl (3S)-3-(4-chlorophenyl)-6-methyl-1,3-dihydrofuro[3,4-c]pyridin-7-yl carbonate, and Methyl 1-[(Z)-({5-[({[(3S)-3-(4-chlorophenyl)-6-methyl-1,3-dihydrofuro[3,4-c]pyridin-7-yl]oxy}carbonyl)oxy]pentyl}oxy)-NNO-azoxy]-prolinate, or a pharmaceutically acceptable salt thereof.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof, are represented.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium (¹H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

The term "alkylene" refers to any divalent linear or branched chain aliphatic hydrocarbon radical having a number of carbon atoms in the specified range. Thus, for example, "—$C_1$-$C_6$ alkylene-" refers to any of the $C_1$ to $C_6$ linear or branched alkylenes, and "—$C_1$-$C_4$ alkylene-" refers to any of the $C_1$ to $C_4$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Another sub-class of interest is an alkylene selected from the group consisting of —$CH_2$—, —$CH(CH_3)$—, and —$C(CH_3)_2$—. Expressions such as "$C_1$-$C_4$ alkylene-phenyl" and "$C_1$-$C_4$ alkyl substituted with phenyl" have the same meaning and are used interchangeably.

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl. The term "phenylene" refers to a divalent phenyl ring radical ($C_6H_4$).

Unless otherwise specifically noted as only "unsubstituted" or only "substituted", alkyl, alkylene and aryl groups are unsubstituted or substituted on each carbon atom, with halo, $C_1$-$C_{20}$ allkyl, $CF_3$, $NH_2$, $N(C_1$-$C_6$ allkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$alkyl)OC(O)—, ($C_0$-$C_6$ allcyl)O($C_1$-$C_6$($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)NH($C_1$-$C_6$ alkyl), —NH($C_1$-$C_6$ alkyl)NHSO$_2$($C_1$-$C_6$ alkyl), —($C_1$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The diuretics of the invention are useful for treating hypertension, pulmonary arterial hypertension, congestive heart failure, conditions resulting from excessive water retention, cardiovascular diseases, diabetes, oxidative stress, endothelial dysfunction, cirrhosis, pre-eclampsia, osteoporosis, or nephropathy, comprising administering a compounds of the invention to a patient having such a condition, or being at risk to having such condition The invention also relates to the use of diuretics of the invention for the preparation of a medicament for the treatment and/or prophylaxis of the above-mentioned diseases.

The above-mentioned diuretics of the invention are also of use in combination with other pharmacologically active compounds comprising angiotensin II receptor antagonists (e.g., losartan, valsartan, candesartan, irbesartan, olmesartan) angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075, 451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S, 5S,7S)—N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, veraparmil, diltiazem, gallopamil, niludipine, nimodipine, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide.

The dosage regimen utilizing the diuretics is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the diuretics, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, and more preferably 25 mg/day to 150 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the diuretics may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The diuretics of the invention can be administered in such oral forms as tablets, capsules and granules. The diuretics are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose aetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

Methods of Synthesis

Several methods for preparing the compounds of this invention are described in the following Schemes and Examples. All variables have their meanings as described above unless otherwise specifically defined. Starting materials and intermediates are made from known procedures or as otherwise illustrated.

Scheme 1 describes a convenient method to prepare 3-(4-chlorophenyl)-6-methyl-1,3-dihydrofuro[3,4-c]pyridin-7-yl carboxylate ester compounds of the general structure 1-3 in this invention. Either racemic or enantiomeric phenol 1-1 is treated with an activated acid 1-2 at an appropriate temperature such as room temperature in the presence of a suitable base such as N,N-diisopropylethylamine, triethylamine, N-methylmorpholine, pyridine, or lutidine in an appropriate solvent such as dichloromethane, chloroform, acetonitrile, tetrahydrofuran, dioxane, toluene, N,N-dimethylformamide, or N-methylpyrrolidinone. Acid chloride 1-2 can be readily formed by treating an appropriate carboxylic acid with an chlorinating reagent such as thionyl chloride, phosphorus trichloride, phosphorus pentachloride, oxalyl chloride in the presence of catalytical amount of Vilsmeier reagent, or triphenylphosphine and carbon tetrachloride or trichloroacetonitrile. Other forms of activated acid 1-2 can be prepared using methods known to those skilled in the art.

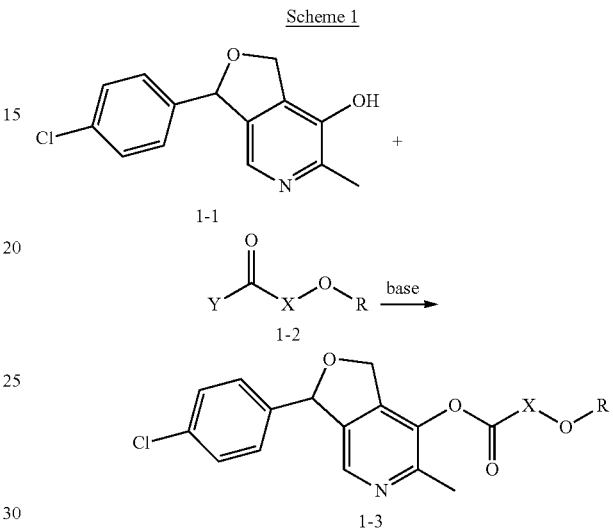

Scheme 1

X is —$C_{1-6}$alkylene- which is unsubstituted or substituted with —$C_{1-6}$ alkyl or —O—$C_{1-6}$ alkyl, or -cyclohexylene- which is unsubstituted or substituted with —$C_{1-6}$ alkyl or —O—$C_{1-6}$ alkyl, or -phenylene- which is unsubstituted or substituted with —$C_{1-6}$ alkyl or —O—$C_{1-6}$ alkyl.

Y is Cl, Br, F, $OC_6F_5$, or N-hydroxysuccinimide.

Scheme 2 delineates an alternative method to prepared 3-(4-chlorophenyl)-6-methyl-1,3-dihydrofuro[3,4-c]pyridin-7-yl carboxylate ester compounds of the general structure 1-3 in this invention. The carboxylic acid 2-1 in this reaction can be activated for acylation at an appropriate temperature such as room temperature with a suitable coupling reagent such as N,N'-dicyclohexylcarbodiimide (DCC), 1-(3-dimethylaminopropyl)-3ethylcarbodiimide (EDC), (benzotriazol-1-yl-oxy)tripyrrolidinophosphonium hexafluorophosphate (PyBOP), bis(2-oxo-3-oxazolidinyl)phosphinic chloride (BOP-Cl), or 1,1'-carbonyldiimidazole in the presence or absence of a base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone.

Scheme 2

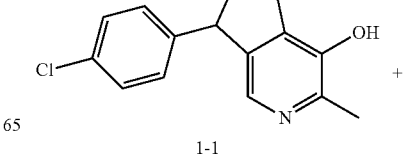

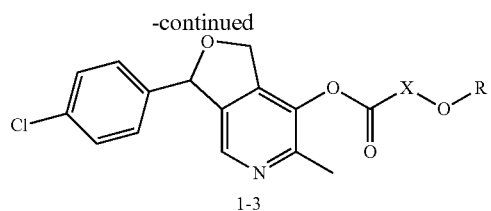

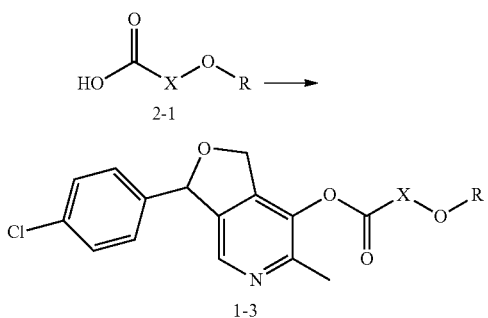

X is —C$_{1-6}$alkylene- which is unsubstituted or substituted with —C$_{1-6}$ alkyl or —O—C$_{1-6}$ alkyl, or -cyclohexylene- which is unsubstituted or substituted with —C$_{1-6}$ alkyl or —O—C$_{1-6}$ alkyl, or -phenylene-which is unsubstituted or substituted with —C$_{1-6}$ alkyl or —O—C$_{1-6}$ alkyl.

Scheme 3 describes a straightforward method to prepare 3-(4-chlorophenyl)-6-methyl-1,3-dihydrofuro[3,4-c]pyridin-7-yl carbonate compounds of the general structure 1-3 in this invention. Either racemic or enantiomeric phenol 1-1 is treated with an activated formate 3-1 at an appropriate temperature such as room temperature in the presence of a suitable base such as N,N-diisopropylethylamine, triethylamine, N-methylmorpholine, pyridine, lutidine, potassium carbonate, sodium carbonate, cesium carbonate, or sodium hydride in an appropriate solvent such as dichloromethane, dichloroethane, chloroform, acetonitrile, tetrahydrofuran, dioxane, toluene, N,N-dimethylformamide, or N-methylpyrrolidinone. The activated formate 3-1 can be prepared by treating an appropriate alcohol at an appropriate temperature such as 0° C. or room temperature with a suitable reagent such as phosgene, trichloromethyl chloroformate, 1,1'-carbonyldiimidazole, p-nitrophenyl chloroformate, trichloroacetyl chloride, or 1-chloroethyl chloroformate in the presence of a suitable base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone.

Scheme 3

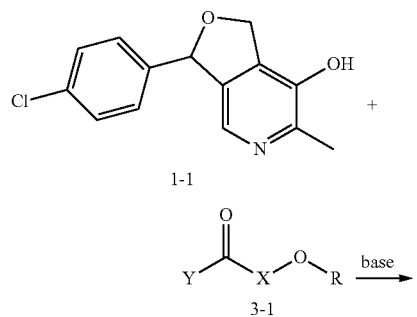

X is —C$_{1-6}$alkylene- which is unsubstituted or substituted with —C$_{1-6}$ alkyl or —O—C$_{1-6}$ alkyl, or -cyclohexylene- which is unsubstituted or substituted with —C$_{1-6}$ alkyl or —O—C$_{1-6}$ alkyl.
Y is Cl, imidazole, p-nitrophenyl, trichloromethyl, or 1-chloroethoxy.

Finally, Scheme 4 describes an alternative method to prepare 3-(4-chlorophenyl)-6-methyl-1,3-dihydrofuro[3,4-c]pyridin-7-yl carbonate compounds of the general structure 1-3 in this invention. In this reaction, an activated formate 4-1 of either racemic or enantiomeric 3-(4-chlorophenyl)-6-methyl-1,3-dihydrofuro[3,4-c]pyridin-7-ol is treated with an appropriate alcohol 4-2 at an appropriate temperature such as room temperature in the presence of a suitable base such as N,N-diisopropylethylamine, triethylamine, N-methylmorpholine, pyridine, lutidine, potassium carbonate, sodium carbonate, cesium carbonate, or sodium hydride in an appropriate solvent such as dichloromethane, dichloroethane, chloroform, acetonitrile, tetrahydrofuran, dioxane, toluene, N,N-dimethylformamide, or N-methylpyrrolidinone. The activated formate 4-1 can be prepared by treating the phenol 1-1 at an appropriate temperature such as 0° C. or room temperature with a suitable reagent such as phosgene, trichloromethyl chloroformate, 1,1'-carbonyldiimidazole, p-nitrophenyl chlorofolutate, trichloroacetyl chloride, or 1-chloroethyl chloroformate in the presence of a suitable base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone.

Scheme 4

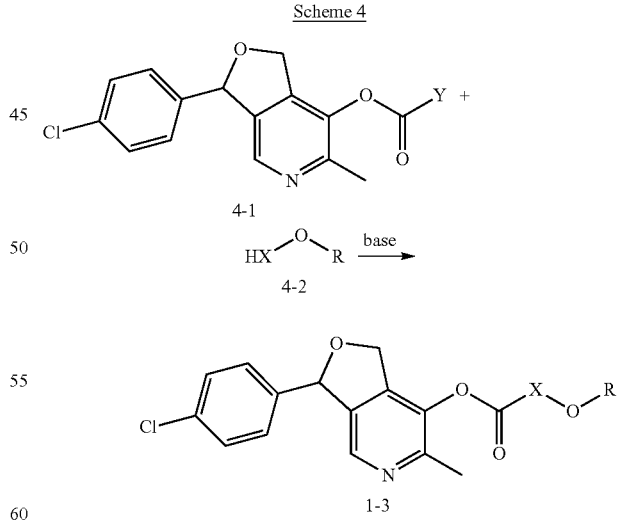

X is —C$_{1-6}$alkylene- which is unsubstituted or substituted with —C$_{1-6}$ alkyl or —O—C$_{1-6}$ alkyl, or -cyclohexylene- which is unsubstituted or substituted with —C$_{1-5}$ alkyl or —O—C$_{1-6}$ alkyl.
Y is Cl, imidazole, p-nitrophenyl, trichloromethyl, or 1-chloroethoxy.

General Procedures.

Reactions sensitive to moisture or air were performed under nitrogen or argon using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 μm 2.1×20 mm column with gradient 10:90-98:2 v/v $CH_3CN/H_2O$+v 0.05% TFA over 3.25 min then hold at 98:2 v/v $CH_3CN/H_2O$+v 0.05% TFA for 0.75 min; flow rate 1.5 mL/min, UV wavelength 254 nm. Two other HPLC conditions applied were noted as LC-1 (Waters C18 XTerra 3.5 μm 2.1×20 mm column with gradient 10:90-98:2 v/v $CH_3CN/H_2O$+v 0.05% TFA over 1.25 min then hold at 98:2 v/v $CH_3CN/H_2O$+v 0.05% TFA for 0.75 min; flow rate 1.5 mL/min, UV wavelength 254 nm) and LC-2 (Waters C18 XTerra 3.5 μm 30×50 mm column with gradient 10:90-98:2 v/v $CH_3CN/H_2O$+v 0.05% TFA over 3.75 min then hold at 98:2 v/v $CH_3CN/H_2O$+v 0.05% TFA for 1.75 min; flow rate 1.0 mL/min, UV wavelength 254 nm). Concentration of solutions was carried out on a rotary evaporator under reduced pressure. Flash chromatography was performed using a Biotage Flash Chromatography apparatus (Dyax Corp.) or a CombiFlash Rf apparatus (Teledyne ISCO) on silica gel (32-63 μM, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz). Chiral analytical chromatography was performed on one of Chiralpak AS, Chiralpak AD, Chiralcel OD, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, or Chiralcel OJ columns (20×250 mm) (Daicel Chemical Industries, Ltd.) with desired isocratic solvent systems identified on chiral analytical chromatography.

Abbreviations: acetic acid (AcOH), aqueous (aq), (benzotriazol-1-yloxy)tripyrrolidino-phosphonium hexafluorophosphate (PyBOP), 4-N,N-dimethylaminopyridine (DMAP), ethyl acetate (EtOAc), diethyl ether (ether or $Et_2O$), N,N-diisopropylethylamine (DIEA), N,N-dimethylformamide (DMF), gram(s) (g), hour(s) (h or hr), microliter(s) (μL), milligram(s) (mg), milliliter(s) (mL), millimole (mmol), mass spectrum (ms or MS), 2-propanol (IPA), retention time ($R_t$), room temperature (rt), saturated aq sodium chloride solution (brine), trifluoroacetic acid (TFA), tetrahydrofuran (THF), and minute(s) (min).

(3S)-3-(4-Chlorophenyl)-6-methyl-1,3-dihydrofuro [3,4-c]pyridin-7-yl 4-[({[(1Z)-2-tert-butyl-2-methyl-1-oxido-1λ$^5$-diazan-1-ylidene]amino}oxy)methyl] benzoate Step A: methyl 4-[({[(1Z)-2-tert-butyl-2-methyl-1-oxido-1λ$^5$-diazan-1-ylidene]amino}oxy)methyl] benzoate To a solution of methyl 4-(bromomethyl)benzoate (677 mg, 2.96 mmol) in DMF (2.5 mL) was added sodium (1Z)-3-tert-butyl-3-methyltriaz-1-en-1-olate 2-oxide (500 mg, 2.96 mmol). The mixture was heated by microwave at 80° C. for 15 min. After cooling down to rt, the mixture was partitioned between $Et_2O$ (50 mL) and water (50 mL). The organic layer was washed with brine (3×50 mL), dried over $MgSO_4$, and concentrated. The residue was purified by flash chromatography (Biotage 25+M) using 20-30% EtOAc/hexane gradient, affording the title compound: $^1$H NMR (500 MHz, $CDCl_3$) δ 7.87 (m, 2H), 7.30 (m, 21-1), 5.16 (s, 21-1), 3.75 (s, 3H), 2.63 (s, 3H), 1.00 (s, 9H).

Step B: 4-[({[(1Z)-2-tert-butyl-2-methyl-1-oxido-1λ$^5$-diazan-1-ylidene]amino}oxy)methyl]benzoic acid To a solution of methyl 4-[({[(1Z)-2-tert-butyl-2-methyl-1-oxido-1λ$^5$-diazan-1-ylidene]amino}oxy)methyl]benzoate (360 mg, 1.22 mmol) in MeOH (10 mL) at rt was added 5N NaOH (0.7 mL, 3.5 mmol). After was stirring at rt over night, the mixture was partitioned between $Et_2O$ (50 mL) and water (50 mL). The organic layer was washed with brine (2×50 mL), dried over $MgSO_4$, and concentrated to give the title compound: $^1$H NMR (500 MHz, $CDCl_3$) δ 8.11 (in, 2H), 7.50 (m, 2H), 5.34 (s, 2H), 2.81 (s, 3H), 1.12 (s, 9H).

Step C: (3S)-3-(4-chlorophenyl)-6-methyl-1,3-dihydrofuro[3,4-c]pyridin-7-yl4-[({[(12)-2-tert-butyl-2-methyl-1-oxide-1λ$^5$-diazan-1-ylidene]amino}oxy) methyl]benzoate To a solution of 4-[({[(1Z)-2-tert-butyl-2-methyl-1-oxido-1λ$^5$-diazan-1-ylidene]amino}oxy)methyl]benzoic acid (320 mg, 1.14 mmol) in DMF (10 mL) at rt was added (3S)-3-(4-chlorophenyl)-6-methyl-1,3-dihydrofuro[3,4-c]pyridine-7-ol (250 mg, 0.96 mmol) and followed by PyBOP (746 mg, 1.43 mmol), $Et_3N$ (242 mg, 2.39 mmol) and DMAP (11.67 mg, 0.1 mmol). After stirring at rt over night, the mixture was partitioned between $Et_2O$ (100 mL) and water (100 mL). The organic layer was washed with brine (3×100 mL), dried over $MgSO_4$, and concentrated. The residue was purified by flash chromatography (Biotage 25+M) using 20-50% EtOAc/hexane gradient, affording the title compound: $^1$H NMR (500 MHz, $CDCl_3$) δ 8.16 (m, 2H), 7.52 (m, 2H), 7.30-7.24 (m, 4H), 6.18 (s, 1H), 5.32 (s, 2H), 5.18-5.07 (m, 2H), 2.76 (s, 3H), 2.46 (s, 3H), 1.14 (s, 9H).

Example 2

Example 1

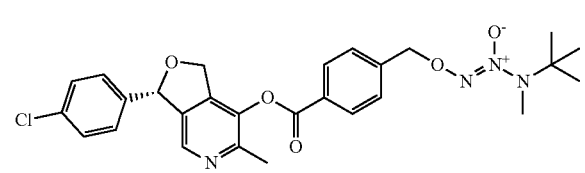 [SMILES: Cc1ncc2c(c1OC(=O)c1ccc(CO/N=[N+](\[O-])N(C)C(C)(C)C)cc1)CO[C@H]2c1ccc(Cl)cc1]

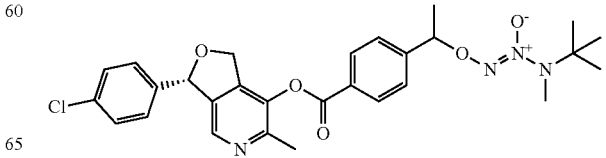

(3S)-3-(4-Chlorophenyl)-6-methyl-1,3-dihydrofuro[3,4-c]pyridin-7-yl 4-[1-({[(1Z)-2-tert-butyl-2-methyl-1-oxido-1λ⁵-diazan-1-ylidene]amino}oxy)ethyl]benzoate This example was prepared using procedures analogous to those described for EXAMPLE 1 substituting methyl 4(1-bromoethyl)benzoate for methyl 4(1-bromomethyl)benzoate in step A. ¹H NMR (500 MHz, CDCl₃) δ 8.18 (m, 2H), 7.52 (m, 2H), 7.32-7.25 (m, 4H), 6.20 (s, 1H), 5.48 (m, 1H), 5.18-5.07 (m, 2H), 2.75 (s, 3H), 2.49 (s, 3H), 1.69 (d, 3H), 1.13 (s, 9H).

Example 3

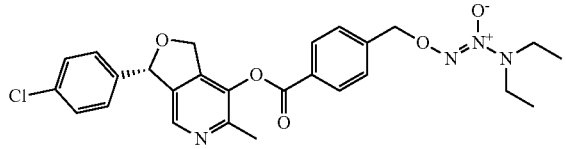 [SMILES: CCN(CC)/[N+]([O-])=N/OCc1ccc(C(=O)Oc2c(C)ncc3c2CO[C@H]3c2ccc(Cl)cc2)cc1]

(3S)-3-(4-Chlorophenyl)-6-methyl-1,3-dihydrofuro[3,4-c]pyridin-7-yl 4-[({[(1Z)-2,2-diethyl-1-oxido-1λ⁵-diazan-1-ylidene]amino}oxy)methyl]benzoate The title compound was made by following the procedures described in EXAMPLE 1 substituting sodium (1Z)-3,3-diethyltriaz-1-en-1-olate 2-oxide for sodium (1Z)-3-tert-butyl-3-methyltriaz-1-en-1-olate 2-oxide in step A: ¹H NMR (500 MHz, CDCl₃) δ 8.21 (m, 2H), 7.58 (m, 2H), 7.36-7.28 (m, 4H), 6.23 (s, 1H), 5.34 (s, 2H), 5.23-5.09 (m, 2H), 3.12 (m, 4H), 2.51 (s, 3H), 1.04 (m, 6H).

Example 4

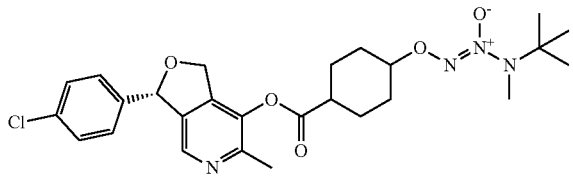 [SMILES: Cc1ncc2c(c1OC(=O)C1CCC(O/N=[N+](\[O-])N(C)C(C)(C)C)CC1)CO[C@H]2c1ccc(Cl)cc1]

(3S)-3-(4-Chlorophenyl)-6-methyl-1,3-dihydrofuro[3,4-c]pyridin-7-yl 4-({[(1Z)-2-tert-butyl-2-methyl-1-oxido-1λ⁵-diazan-1-ylidene]amino}oxy)cyclohexanecarboxylate Step A: ethyl 4-iodocyclohexanecarboxylate To a solution of ethyl 4-hydroxycyclohexane carboxylate (10.0 g, 58.1 mmol) in CH₂Cl₂ (200 mL) at 0° C. was added imidazole (11.86 g, 174.0 mmol), triphenylphosphine (25.9 g, 99.0 mmol), and followed by iodine (25.05 g, 99.0 mmol) several portions over a period of 45 min. The resulting suspension was gradually allowed to warm up to rt. After stirring at rt over night, the mixture was partitioned between Et₂O (200 mL) and water (200 mL). The organic layer was washed with saturated Na₂S₂O₃ (100 mL) and brine (3×100 mL), dried over MgSO₄, and concentrated. The residue was purified by flash chromatography (Biotage 40+M) using 10-20% EtOAc/hexane gradient, affording the title compound: ¹H NMR (500 MHz, CDCl₃) δ 5.70 (m, 1H), 4.20-4.10 (m, 2H), 2.58 (m, 1H), 2.48-1.60 (m, 8H), 1.28 (m, 3H).

Step B: (3S)-3-(4-chlorophenyl)-6-methyl-1,3-dihydrofuro[3,4-c]pyridin-7-yl 4-({[(1Z)-2-tert-butyl-2-methyl-1-oxido-1λ⁵-diazan-1-ylidene]amino}oxy)cyclohexanecarboxylate The title compound was made by following the procedures described in EXAMPLE 1 substituting ethyl 4-iodocyclohexanecarboxylate for methyl 4-(bromomethyl)benzoate in step A: ¹H NMR (500 MHz, CDCl₃) δ 8.03 (s, 1H), 7.32-7.24 (m, 4H), 6.18 (s, 1H), 5.12-4.98 (m, 2H), 4.30 (in, 1H), 2.81 (s, 3H), 2.64 (m, 1H), 2.42 (s, 3H), 2.28 (m, 4H), 2.70 (m, 4H), 1.23 (s, 9H).

The following diastereomers of Example 4 were separated by chiral chromatography with conditions as indicated:

| Example Number | Name | HPLC/MS m/z (M + 1) R_t (min) (LC-2) | |
|---|---|---|---|
| Example 5 | (3S)-3-(4-Chlorophenyl)-6-methyl-1,3-dihydrofuro[3,4-c]pyridin-7-yl cis-4-({[(1Z)-2-tert-butyl-2-methyl-1-oxidohydrazono]amino}oxy)cyclohexanecarboxylate | 517.3 3.52 | 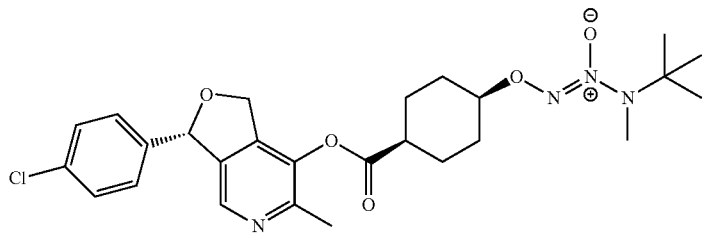 [SMILES: Cc1ncc2c(c1OC(=O)[C@H]1CC[C@@H](O/N=[N+](\[O-])N(C)C(C)(C)C)CC1)CO[C@H]2c1ccc(Cl)cc1] (fast isomer, OD 25% IPA/heptane) |

| Example Number | Name | HPLC/MS m/z (M + 1) R$_t$ (min) (LC-2) | |
|---|---|---|---|
| Example 6 | (3S)-3-(4-Chlorophenyl)-6-methyl-1,3-dihydrofuro[3,4-c]pyridin-7-yl trans-4-({[(1Z)-2-tert-butyl-2-methyl-1-oxidohydrazono]amino}oxy)cyclohexanecarboxylate | 517.3 3.52 | 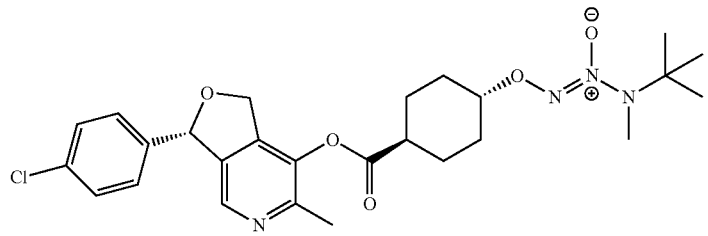 [SMILES: Cc1ncc2c(c1OC(=O)[C@H]1CC[C@H](O/N=[N+](\[O-])N(C)C(C)(C)C)CC1)CO[C@H]2c1ccc(Cl)cc1] |

(slow isomer, OD 25% IPA/heptane)

Example 7

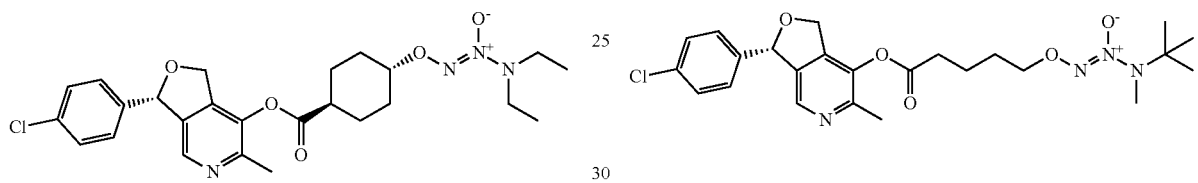

(3S)-3-(4-Chlorophenyl)-6-methyl-1,3-dihydrofuro [3,4-c]pyridin-7-yl trans-4-({[(1Z)-2,2-diethyl-1-oxido-1λ$^5$-diazan-1-ylidene]amino}oxy)cyclohexanecarboxylate

Step A: methyl trans-4-hydroxycyclohexanecarboxylate

To a solution of trans-4-hydroxycyclohexanecarboxylic acid (1.0 g, 6.94 mmol) in CH$_2$Cl$_2$ (15 mL) at 0° C. was added 2.0M TMS-diazomethane in hexane (11.0 mL, 22.0 mmol). The mixture was allowed to gradually warm to rt. After stirring at rt over night, the mixture was concentrated and the residue was purified by flash chromatography (Biotage 25+M) using 30-50% EtOAc/hexane gradient, affording the title compound.

Step B: (3S)-3-(4-chlorophenyl)-6-methyl-1,3-dihydrofuro[3,4-c]pyridin-7-yl trans-4-({[(1Z)-2,2-diethyl-1-oxido-1λ$^5$-diazan-1-ylidene]amino}oxy)cyclohexanecarboxylate The title compound was made by following the procedures described in EXAMPLE 4 substituting methyl trans-4-hydroxycyclohexane carboxylase for ethyl 4-hydroxycyclohexanecarboxylate and sodium (1Z)-3,3-diethyltriaz-1-en-1-olate 2-oxide for sodium (1Z)-3-text-butyl-3-methyltriaz-1-en-1-olate 2-oxide in step A: $^1$H NMR (500 MHz, CDCl$_3$) δ 8.04 (s, 1H), 7.34-7.24 (m, 4H), 6.18 (s, 1H), 5.13-4.99 (m, 2H), 4.33 (m, 1H), 3.08 (m, 4H), 2.65 (m, 1H), 2.43 (s, 3H), 2.28 (m, 4H), 1.70 (m, 4H), 1.09 (m, 6H).

Example 8

(3S)-3-(4-Chlorophenyl)-6-methyl-1,3-dihydrofuro [3,4-c]pyridin-7-yl 5-({[(1Z)-2-tert-butyl-2-methyl-1-oxido-1λ$^5$-diazan-1-ylidene]amino}oxy)pentanoate

Step A: 5-({[(1Z)-2-tert-butyl-2-methyl-1-oxido-1λ$^5$-diazan-1-ylidene]amino}oxy)pentanoic acid To a solution of 5-({ [(1Z)-2-tert-butyl-2-methyl-1-oxido-1λ$^5$-diazan-1-ylidene]amino}oxy)pentan-1-ol (370 mg, 1.59 mmol) and sodium periodate (1.02 g, 4.76 mmol) in 18 mL of CH$_3$CN/CHCl$_3$/H$_2$O (1:1:1) was added ruthenium(III) chloride hydrate (32 mg, 0.24 mmol). After stirring at rt over night, the mixture was extracted with CH$_2$Cl$_2$ (3×50 mL), dried over MgSO$_4$ and concentrated to give the title product, which was used directly.

Step B: (3S)-3-(4-chlorophenyl)-6-methyl-1,3-dihydrofuro[3,4-c]pyridin-7-yl 5-({[(1Z)-2-tert-butyl-2-methyl-1-oxido-1λ$^5$-diazan-1-ylidene]amino}oxy)pentanoate The title compound was made by following the procedures described in EXAMPLE 1 substituting 5-({[(1Z)-2-tert-butyl-2-methyl-1-oxide-1λ$^5$-diazan-1-ylidene]amino}oxy) pentanoic acid for 4-[({[(1Z)-2-tert-butyl-2-methyl-1-oxido-1λ$^5$-diazan-1-ylidene]amino}oxy)methyl]benzoic acid in step C: $^1$H NMR (500 MHz, CDCl$_3$) δ 8.04 (s, 1H), 7.34-7.24 (m, 4H), 6.18 (s, 1H), 5.15-5.01 (m, 2H), 4.32 (m, 2H), 2.81 (s, 3H), 2.67 (m, 2H), 2.43 (s, 3H), 1.90 (m, 4H), 1.23 (s, 9H).

Example 9

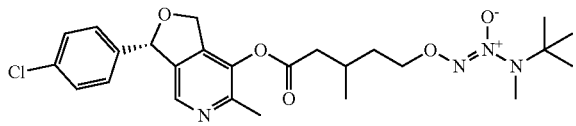 [SMILES: Cc1ncc2c(c1OC(=O)CCCCO/N=[N+](\[O-])N(C)C(C)(C)C)CO[C@H]2c1ccc(Cl)cc1]

(3S)-3-(4-Chlorophenyl)-6-methyl-1,3-dihydrofuro[3,4-c]pyridin-7-yl 5-({[(1Z)-2-tert-butyl-2-methyl-1-oxido-1λ⁵-diazan-1-ylidene]amino}oxy)-3-methylpentanoate

Step A: 5-iodo-3-methylpentan-1-ol

To a solution of 3-methyl-1,5-pentanediol (5.05 g, 42.7 mmol) in $CH_3CN$ (50 mL) was added sodium iodide (9.62 g, 64.1 mmol) and then zirconium(IV) chloride (4.98 g, 21.4 mmol). The mixture was heated at 90° C. for 20 min. After cooling down to rt, the mixture was partitioned between $Et_2O$ (200 mL) and water (200 mL). The organic layer was washed with brine (3×100 mL), dried over $MgSO_4$, and concentrated. The residue was purified by flash chromatography (Biotage 40+M) using 10-20% EtOAc/hexane gradient, affording the title compound: $^1H$ NMR (500 MHz, $CDCl_3$) δ 3.68 (m, 2H), 3.30-3.16 (m, 2H), 1.90 (m, 1H), 1.78-1.60 (m, 4H), 1.44 (s, 1H), 0.93 (d, J=6.4 Hz, 3H).

Step B: 5-({[(1E)-2-tert-butyl-2-methyl-1-oxidohydrazono]amino}oxy)-3-methylpentan-1-ol The title compound was made by following the procedures described in EXAMPLE 1 substituting 5-iodo-3-methylpentan-1-ol for methyl 4-(bromomethyl)benzoate in step A: $^1H$ NMR (500 MHz, $CDCl_3$) δ 4.35 (m, 2H), 3.70 (m, 2H), 2.80 (s, 3H), 1.80 (m, 2H), 1.62 (m, 2H), 1.50 (m, 1H), 1.26 (s, 9H), 0.99 (d, 6.6 Hz, 3H).

Step C: (3S)-3-(4-chlorophenyl)-6-methyl-1,3-dihydrofuro[3,4-c]pyridin-7-yl 5-({[(1Z)-2-tert-butyl-2-methyl-1-oxido-1λ⁵-diazan-1-ylidene]amino}oxy)-3-methylpentanoate The title compound was made by following the procedures described in EXAMPLE 8 substituting 5-({[(1E)-2-tert-butyl-2-methyl-1-oxidohydrazono]amino}oxy)-3-methylpentan-1-ol for 5-({[(1Z)-2-tert-butyl-2-methyl-1-oxido-1λ⁵-diazan-1-ylidene]amino}oxy)pentan-1-ol in step A: $^1H$ NMR (500 MHz, $CDCl_3$) δ 7.97 (s, 1H), 7.26-7.20 (m, 4H), 6.11 (s, 1H), 5.10-4.94 (m, 2H), 4.28 (m, 2H), 2.72 (s, 3H), 2.62 (m, 1H), 2.45 (m, 1H), 2.37 (s, 3H), 2.12 (m, 1H), 1.89 (m, 1H), 1.15 (s, 9H), 1.04 (d, J=6.6 Hz, 3H).

Example 10

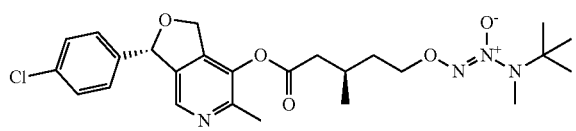 [SMILES: Cc1ncc2c(c1OC(=O)C[C@H](C)CCO/N=[N+](\[O-])N(C)C(C)(C)C)CO[C@H]2c1ccc(Cl)cc1]

(3S)-3-(4-Chlorophenyl)-6-methyl-1,3-dihydrofuro[3,4-c]pyridin-7-yl (3R)-5-({[(1Z)-2-tert-butyl-2-methyl-1-oxido-1λ⁵-diazan-1-ylidene]amino}oxy)-3-methylpentanoate

Step A: methyl (3R)-5-hydroxy-3-methylpentanoate

To a solution of (3R)-5-methoxy-3-methyl-5-oxopentanoic acid (2.2 g, 13.7 mmol) in THF (20 mL) at rt was added 5.0 M $BH_3.Me_2S$ in THF (4.0 mL, 20.0 mmol). After stirring at it over night, the mixture was concentrated to give the title product, which was used directly.

Step B: methyl (3R)-3-methyl-5-(methylsulfonyl)-5-oxopentanoate

To a solution of methyl (3R)-5-hydroxy-3-methylpentanoate (2.1 g, 14.37 mmol) in $Et_2O$ (10 mL) and $Et_3N$ (1.45 g, 14.37 mmol) at 0° C. was added methylsulfonyl chloride (1.65 g, 14.37 mol). After stirring at 0° C. for 1 h, solid was filtered off and the filtrate was concentrated to give the title product, which was used directly.

Step C: (3S)-3-(4-chlorophenyl)-6-methyl-1,3-dihydrofuro[3,4-c]pyridin-7-yl (3R)-5-({[(1Z)-2-tert-butyl-2-methyl-1-oxido-1λ⁵-diazan-1-ylidene]amino}oxy)-3-methylpentanoate This title compound was made by following the procedures described in EXAMPLE 1 substituting methyl (3R)-3-methyl-5-(methylsulfonyl)-5-oxopentanoate for methyl 4-(bromomethyl)benzoate in step A: $^1H$ NMR (500 MHz, $CDCl_3$) δ 7.97 (s, 1H), 7.26-7.20 (m, 4H), 6.11 (s, 1H), 5.10-4.94 (m, 2H), 4.28 (m, 2H), 2.72 (s, 3H), 2.62 (m, 1H), 2.45 (m, 1H), 2.37 (s, 3H), 2.12 (m, 1H), 1.89 (m, 1H), 1.15 (s, 9H), 1.04 (d, J=6.6 Hz, 3H).

Example 11

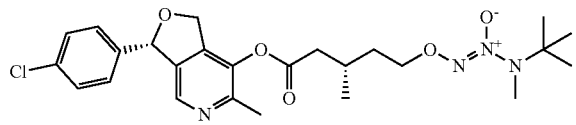

(3S)-3-(4-Chlorophenyl)-6-methyl-1,3-dihydrofuro[3,4-c]pyridin-7-yl (3S)-5-({[(1Z)-2-tert-butyl-2-methyl-1-oxido-1λ⁵-diazan-1-ylidene]amino}oxy)-3-methylpentanoate EXAMPLE 9 as a racemic mixture was resolved by 4.6× 250 mm ChiralPak IC column with 40% $IPA/CO_2$ to afford EXAMPLE 11 at retention time 4.29 min and EXAMPLE 10 at retention time 5.08 min.

Example 12

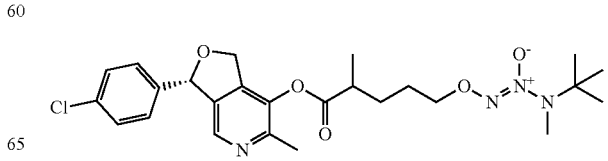

(3S)-3-(4-Chlorophenyl)-6-methyl-1,3-dihydrofuro[3,4-c]pyridin-7-yl 5-({[(1Z)-2-tert-butyl-2-methyl-1-oxido-1λ⁵-diazan-1-ylidene]amino}oxy)-2-methylpentanoate Step A: ethyl 5-iodo-2-methylpentanoate To a solution of ethyl 2-methyl-4-pentenoate (8.53 g, 60 mmol) in THF (25 mL) at 0° C. was added 1.0 M BH$_3$.THF in THF (25 mL, 25 mmol). After heating at 50° C. for 1 h, the mixture was cooled to rt, to which a solution of sodium acetate (4.92 g, 60 mmol) in CH$_3$OH (60 mL) was added and followed by iodine monochloride (6.49 g, 40 mmol). After stirring at rt for 45 min, the reaction was quenched by addition of water (100 mL) and saturated Na$_2$S$_2$O$_3$ (50 mL). The mixture was extracted with Et$_2$O (3×100 mL), dried over MgSO$_4$, and concentrated. The residue was purified by flash chromatography (Biotage 40+M) using 10-20% EtOAc/hexane gradient, affording the title compound: $^1$H NMR (500 MHz, CDCl$_3$) δ 4.18 (m, 2H), 3.20 (m, 2H), 2.44 (m, 1H), 1.84 (m, 2H), 1.79 (m, 1H), 1.58 (m, 1H), 1.30 (m, 3H), 1.19 (d, J=6.9 Hz, 3H).

Step B: (3S)-3-(4-chlorophenyl)-6-methyl-1,3-dihydrofuro[3,4-c]pyridin-7-yl 5-({[(1Z)-2-tert-butyl-2-methyl-1-oxido-1λ⁵-diazan-1-ylidene]amino}oxy)-2-methylpentanoate The title compound was made by following the procedures described in EXAMPLE 1 substituting ethyl 5-iodo-2-methylpentanoate for methyl 4-(bromomethyl)benzoate in step A: $^1$H NMR (500 MHz, CDCl$_3$) δ 7.97 (s, 1H), 7.27-7.19 (m, 4H), 6.12 (s, 1H), 5.09-4.94 (m, 2H), 4.25 (m, 2H), 2.73 (s, 3H), 2.37 (s, 3H), 1.82 (m, 4H), 1.62 (m, 1H), 1.29 (d, J=6.8 Hz, 3H), 1.16 (s, 9H), 1.04 (d, J=6.6 Hz, 3H).

Example 13

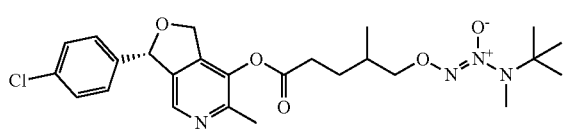 [SMILES: Cc1ncc2c(c1OC(=O)CCC(C)CO/N=[N+](\[O-])N(C)C(C)(C)C)CO[C@H]2c1ccc(Cl)cc1]

(3S)-3-(4-Chlorophenyl)-6-methyl-1,3-dihydrofuro[3,4-c]pyridin-7-yl 5-({[(1Z)-2-tert-butyl-2-methyl-1-oxido-1λ⁵-diazan-1-ylidene]amino}oxy)-4-methylpentanoate The title compound was made by following the procedures described in EXAMPLE 12 substituting ethyl 4-methyl-4-pentenoate for ethyl 2-methyl-4-pentenoate in step A: $^1$H NMR (500 MHz, CDCl$_3$) δ 7.96 (s, 1H), 7.24-7.16 (m, 4H), 6.09 (s, 1H), 5.08-4.92 (m, 2H), 4.06 (d, J=6.7 Hz 2H), 2.70 (s, 3H), 2.60 (m, 2H), 2.35 (s, 3H), 2.00 (m, 1H), 1.90 (m, 1H), 1.60 (m, 1H), 1.13 (s, 9H), 0.95 (d, J=6.9 Hz, 3H).

Example 14

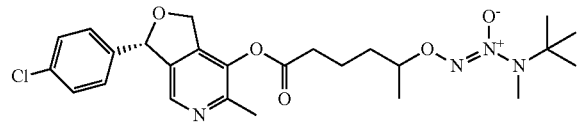 [SMILES: Cc1ncc2c(c1OC(=O)CCCC(C)O/N=[N+](\[O-])N(C)C(C)(C)C)CO[C@H]2c1ccc(Cl)cc1]

(3S)-3-(4-Chlorophenyl)-6-methyl-1,3-dihydrofuro[3,4-c]pyridin-7-yl 5-({[(1Z)-2-tert-butyl-2-methyl-1-oxido-1λ⁵-diazan-1-ylidene]amino}oxy)hexanoate Step A: 5-bromopentan-1-ol To a solution of 1,5-hexanediol (7.0 g, 59.2 mmol) in CH$_2$Cl$_2$ (100 mL) at 0° C. was slowly added BBr$_3$ (22.26 g, 89.0 mmol). After stirring at 0° C. for 30 min, the reaction was then quenched by slowly adding water (150 mL). The mixture was extracted with CH$_2$Cl$_2$ (3×200 mL), dried over MgSO$_4$, and concentrated to give the title product, which was used directly.

Step B: 5-({[(1Z)-2-tert-butyl-2-methyl-1-oxido-1λ⁵-diazan-1-ylidene]amino}oxy)hexan-1-ol To a solution of 5-bromopentan-1-ol (1.2 g, 6.63 mmol) in DMF (2.5 mL) was added sodium (1Z)-3-tert-butyl-3-methyltriaz-1-en-1-olate 2-oxide (1.12 g, 6.63 mmol). The mixture was heated by microwave at 100° C. for 15 min. After cooling down to rt, the mixture was partitioned between Et$_2$O (50 mL) and water (50 mL). The organic layer was washed with brine (3×50 mL), dried over MgSO$_4$, and concentrated. The residue was purified by flash chromatography (Biotage 25+M) using 20-30% EtOAc/hexane gradient, affording the title compound: $^1$H NMR (500 MHz, CDCl$_3$) δ 4.40 (m, 1H), 3.60 (m, 2H), 2.77 (s, 3H), 2.20 (m, 1H), 1.80 (in, 2H), 1.60-1.40 (m, 4H), 1.31 (d, J=6.4 Hz, 3H), 1.20 (s, 9H).

Step C: (3S)-3-(4-chlorophenyl)-6-methyl-1,3-dihydrofuro[3,4-c]pyridin-7-yl 5-({[(1Z)-2-tert-butyl-2-methyl-1-oxido-1λ⁵-diazan-1-ylidene]amino}oxy)hexanoate The title compound was made by following the procedures described in EXAMPLE 8 substituting 5-({[(1Z)-2-tert-butyl-2-methyl-1-oxido-1λ⁵-diazan-1-ylidene]amino}oxy)hexan-1-ol for 5-({[(1Z)-2-tert-butyl-2-methyl-1-oxido-1λ⁵-diazan-1-ylidene]amino}oxy)pentan-1-ol in step A: $^1$H NMR (500 MHz, CDCl$_3$) δ 8.05 (s, 1H), 7.36-7.26 (m, 4H), 6.20 (s, 1H), 5.17-5.02 (m, 2H), 4.50 (m, 1H), 2.82 (s, 3H), 2.67 (m, 2H), 2.44 (s, 3H), 1.90 (m, 4H), 1.90 (m, 1H), 1.78 (m, 1H), 1.41 (m, 3H), 1.24 (s, 9H).

Example 15

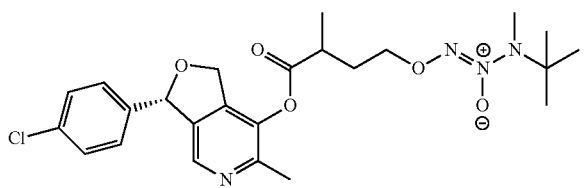 [SMILES: Cc1ncc2c(c1OC(=O)C(C)CCO/N=[N+](\[O-])N(C)C(C)(C)C)CO[C@H]2c1ccc(Cl)cc1]

(3S)-3-(4-Chlorophenyl)-6-methyl-1,3-dihydrofuro
[3,4-c]pyridin-7-yl4-({[(1E)-2-tert-butyl-2-methyl-1-
oxidohydrazono]amino}oxy)-2-methylbutanoate Step A: ethyl 4-bromo-2-methylbutanoate To a HBr saturated solution of EtOH (100 mL) at 0° C. was added α-methyl-γ-butyrolactone (3.0 mL, 31.7 mmol). The mixture was allowed to stir at rt for 3 days and then poured onto ice (500 g). After warming to rt, the mixture was extracted with Et$_2$O (2×200 mL). The combined organic layer was further washed with H$_2$O (300 mL) sat. NaHCO$_3$ (3×300 mL) and brine (300 mL), dried over MgSO$_4$, and concentrated to give the title compound, which was used without further purification: $^1$H NMR (500 MHz, CDCl$_3$) δ 4.15 (q, J=7.1 Hz, 2H), 3.43 (dt, J=1.1, 6.9 Hz, 2H), 2.68 (m, 1H), 2.26 (m, 2H), 1.93 (m, 2H), 1.26 (t, J=7.0 Hz, 3H), 1.19 (d, J=7.1 Hz, 3H).

Step B: (3S)-3-(4-chlorophenyl)-6-methyl-1,3-dihydrofuro[3,4-c]pyridin-7-yl 4-({[(1E)-2-tert-butyl-2-methyl-1-oxidohydrazono]amino}oxy)-2-methylbutanoate The title compound was made by following the procedures described in EXAMPLE 1 substituting ethyl 4-bromo-2-methylbutanoate for methyl 4-(bromomethyl)benzoate in Step A: $^1$H NMR (500 MHz, CDCl$_3$) δ 8.05 (s, 1H), 7.35 (m, 2H), 7.34 (m, 2H), 6.20 (s, 1H), 5.17-5.13 (m, 1H), 5.05-5.01 (m, 1H), 4.40-4.36 (m, 2H), 3.01-2.96 (m, 1H), 2.81 (br. s, 3H), 2.44 (s, 3H), 2.35-2.30 (m, 1H), 2.04-1.97 (m, 1H), 1.41 (d, J=6.9 Hz, 3H), 1.24 (s, 9H).

Example 16

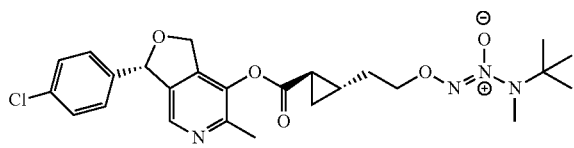 [SMILES: Cc1ncc2c(c1OC(=O)[C@@H]1C[C@H]1CCO/N=[N+](\[O-])N(C)C(C)(C)C)CO[C@H]2c1ccc(Cl)cc1]

(3S)-3-(4-Chlorophenyl)-6-methyl-1,3-dihydrofuro
[3,4-c]pyridin-7-yl 2-[2-({[(1Z)-2-tert-butyl-2-methyl-1-oxidohydrazono]amino}oxy)ethyl]-trans-cyclopropanecarboxylate Step A: ethyl 2-(2-bromoethyl)cyclopropanecarboxylate To a suspension of 4-bromobut-1-ene (10 mL, 99 mmol) and rhodium(II) acetate dimmer (435 mg, 0.99 mmol) in Et$_2$O (450 mL) at rt was added dropwise a solution of ethyl diazoacetate (12.1 mL, 100 mmol) in Et$_2$O (50 mL) over 10 h. After stirring at rt overnight, the mixture was filtered through a cake of Celite and the filtrate was concentrated to give crude title compound, which was used without further purification.

Step B: ethyl 2-[2-({[(1Z)-2-tert-butyl-2-methyl-1-oxidahydrazono]amino}oxy)ethyl]-trans-cyclopropanecarboxylate and ethyl 2-[2-({[(1Z)-2-tert-butyl-2-methyl-1-oxidahydrazono]amino}oxy)ethyl]-cis-cyclopropanecarboxylate To a solution of ethyl 2-(2-bromoethyl)cyclopropanecarboxylate (16.9 g, 76 mmole) in DMF (100 mL) was added sodium (1Z)-3-tert-butyl-3-methyltriaz-1-en-1-olate 2-oxide (15.5 g, 92 mmol). The mixture was heated by microwave at 80° C. for 15 min. After cooling down to rt, the mixture was partitioned between Et$_2$O (300 mL) and water (300 mL). The organic layer was washed with brine (3×300 mL), dried over MgSO4, filtered and concentrated. The residue was purified by flash chromatography (Biotage 25+M) using 5-20% EtOAc/hexane gradient, affording the title compound ethyl 2-[2-({[(1Z)-2-tert-butyl-2-methyl-1-oxidahydrazono] amino}oxy)ethyl]-cis-cyclopropanecarboxylate as less polar fraction: $^1$H NMR (500 MHz, CDCl$_3$) δ 4.30-4.28 (m, 2H), 4.13 (q, J=7.1 Hz, 2H), 2.81 (s, 3H), 2.06-1.97 (m, 2H), 1.74-1.65 (m, 1H), 1.39-1.28 (m, 1H), 1.27-1.21 (m, 12H), 1.09-1.05 (m, 1H), 0.98-0.94 (m, 1H); and title compound ethyl 2-[2-({[(1Z)-2-tert-butyl-2-methyl-1-oxidahydrazono] amino}oxy)ethyl]-trans-cyclopropanecarboxylate as polar fraction: $^1$H NMR (500 MHz, CDCl$_3$) δ 4.32 (t, J=7.0 Hz, 2H), 4.11 (q, J=7.1 Hz, 2H), 2.81 (s, 3H), 1.84-1.81 (m, 1H), 1.72-1.67 (m, 1H), 1.44-1.41 (m, 2H), 1.29-1.15 (m, 13H), 0.77-0.73 (m, 1H).

Step C: (3S)-3-(4-chlorophenyl)-6-methyl-1,3-dihydrofuro[3,4-c]pyridin-7-yl 2-[2-({[(1Z)-2-tert-butyl-2-methyl-1-oxidohydrazono]amino}oxy)ethyl]-trans-cyclopropanecarboxylate The title compound was made by following the procedures described in EXAMPLE 1 substituting ethyl 2-[2-({[(1Z)-2-tert-butyl-2-methyl-1-oxidahydrazono]amino}oxy)ethyl]-trans-cyclopropanecarboxylate for methyl 4-[({[(1Z)-2-tert-butyl-2-methyl-1-oxido-1λ$^5$-diazan-1-ylidene]amino}oxy) methyl]benzoate in step B: $^1$H NMR (500 MHz, CDCl$_3$) δ 8.04 (s, 1H), 7.35 (m, 2H), 7.27 (m, 2H), 6.19 (s, 1H), 5.18-5.12 (m, 1H), 5.07-5.01 (m, 1H), 4.40-4.34 (m, 2H), 2.81 (s, 3H), 2.46 (s, 3H), 2.11-2.06 (m, 2H), 1.68-1.64 (m, 1H), 1.36-1.31 (m, 1H), 1.27-1.24 (m, 10H), 1.16-1.12 (m, 1H).

Example 17

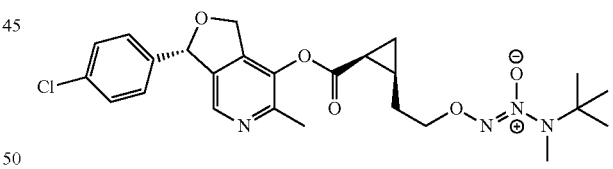

(3S)-3-(4-Chlorophenyl)-6-methyl-1,3-dihydrofuro
[3,4-c]pyridin-7-yl2-[2-({[(1Z)-2-tert-butyl-2-methyl-1-oxidohydrazono]amino}oxy)ethyl]-cis-cyclopropanecarboxylate The title compound was made by following the procedures described in EXAMPLE 1 substituting ethyl 2-[2-({[(1Z)-2-tert-butyl-2-methyl-1-oxidahydrazono]amino}oxy)ethyl] cis-cyclopropanecarboxylate (From EXAMPLE 16, Step B) for methyl 4-[({[(1Z)-2-tert-butyl-2-methyl-1-oxido-1λ$^5$-diazan-1-ylidene]amino}oxy)methyl]benzoate in step B: $^1$H NMR (500 MHz, CDCl$_3$) δ 8.03 (s, 1H), 7.35-7.33 (m, 2H), 7.27-7.25 (m, 2H), 6.18 (s, 1H), 5.17-5.14 (m, 1H), 5.05-5.02 (m, 1H), 4.39 (t, J=6.5 Hz, 2H), 2.81 (s, 3H), 2.45 (s, 3H), 1.91-1.83 (m, 2H), 1.77-1.73 (m, 1H), 1.70-1.64 (m, 1H), 1.44-1.40 (m, 1H), 1.24 (s, 9H), 1.04-1.00 (m, 1H).

Example 18

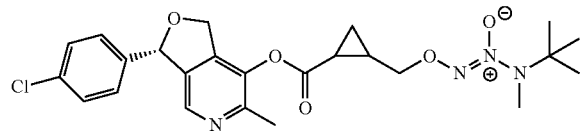 [SMILES: Cc1ncc2c(c1OC(=O)C1CC1CO/N=[N+](\[O-])N(C)C(C)(C)C)CO[C@H]2c1ccc(Cl)cc1]

(3S)-3-(4-Chlorophenyl) 6methyl-1,3-dihydrofuro[3,4-c]pyridin-7-yl 2-[({[2-tert-butyl-2-methyl-1-oxido-1λ$^5$-diazan-1-ylidene]amino}oxy)methyl]cyclopropanecarboxylate Step A: ethyl 2-(hydroxymethyl)cyclopropanecarboxylate Sodium borohydride (1.89 g, 49.9 mmol) was added to a solution of ethyl 2-formyl-1-cyclopropanecarboxylate (7.1 g, 49.9 mmol) in methanol (100 ml) at 0° C. The solution was stirred at 0° C. for 1 hour. The solvent was removed in vacuo. Brine was added and the solution was extracted with chloroform (2×50 mL). The combined organic layers were dried (magnesium sulfate), filtered, and concentrated in vacuo to give the title compound as a colorless oil. $^1$H NMR (500 MHz, CHCl$_3$) δ 4.13-4.06 (m, 2H), 3.63-3.56 (m, 1H), 3.48-3.41 (m, 1H), 1.97 (br s, 1H), 1.74-1.66 (m, 1H), 1.55 (dt, J=8.7, 4.2 Hz, 1H), 1.24 (t, J=7.2 Hz, 3H), 1.19 (dt, J=8.9, 4.7 Hz, 1H), 0.88-0.82 (m, 1H).

Step B: ethyl 2-(bromomethyl)cyclopropanecarboxylate

Bromine (8.28 mL, 161 mmol) was added dropwise to a solution of ethyl 2-(hydroxymethyl)cyclopropanecarboxylate (23.17 g, 161 mmol) and triphenylphosphine (42.2 g, 161 mmol) in DMF (230 mL). The solution was stirred at rt for 1 hr. Saturated aqueous sodium bicarbonate solution was added, and the solution was extracted with ether (2×300 mL). The combined organic layers were dried (magnesium sulfate), filtered, and concentrated in vacua. The residue was purified by silica gel chromatography, eluting with 0-30% ethyl acetate/hexanes to give the title compound as a colorless oil. $^1$H NMR (500 MHz, CDCl$_3$) δ 4.13 (q, J=7.2 Hz, 2H), 3.36 (dd, J=10.5, 7.3 Hz, 1H), 3.30 (dd, J=10.5, 7.5 Hz, 1H), 1.94-1.85 (m, 1H), 1.64 (dt, J=8.6, 4.5 Hz, 1H), 1.42-1.36 (m, 1H), 1.26 (t, J=7.2 Hz, 3H), 0.97-0.91 (m, 1H).

Step C: (3S)-3-(4-chlorophenyl)-6-methyl-1,3-dihydrofuro[3,4-c]pyridin-7-yl 2-[({[2-tert-butyl-2-methyl-1-oxido-1λ$^5$-diazan-1-ylidene]amino}oxy)methyl]cyclopropanecarboxylate The title compound was made by following the procedures described in EXAMPLE 1 substituting ethyl 2-(bromomethyl)cyclopropanecarboxylate for methyl 4-(bromomethyl)benzoate in step A. The two diastereomers were separated by supercritical fluid chromatography (Chiralpak AD) eluting with 30% methanol in supercritical CO$_2$:

| Example Number | Elution Order | $^1$H NMR (500 MHz, CHCl$_3$) δ |
|---|---|---|
| Example 19 | fast | 8.04 (s, 1H), 7.34 (d, J = 8.0 Hz, 2H), 7.26 (d, J = 8.1 Hz, 2H), 6.18 (s, 1H), 5.14 (d, J = 13.8 Hz, 1H), 5.02 (d, J = 13.8 Hz, 1H), 4.33 (dd, J = 12.1, 6.3 Hz, 1H), 4.16 (dd, J = 12.0, 7.5 Hz, 1H), 2.83 (s, 3H), 2.44 (s, 3H), 2.16-2.06 (m, 1H), 2.06-1.96 (m, 1H), 1.55-1.42 (m, 1H), 1.35-1.15 (m, 10H). |
| Example 20 | slow | 8.05 (s, 1H), 7.35 (d, J = 8.1 Hz, 2H), 7.26 (d, J = 8.2 Hz, 2H), 6.19 (s, 1H), 5.14 (d, J = 13.7 Hz, 1H), 5.03 (d, J = 13.8 Hz, 1H), 4.33 (dd, J = 12.1, 6.4 Hz, 1H), 4.17 (dd, J = 12.1, 7.5 Hz, 1H), 2.84 (s, 3H), 2.45 (s, 3H), 2.24-2.00 (m, 1H), 2.02 (dt, J = 8.4, 4.5 Hz, 1H), 1.49 (dt, J = 9.0, 4.9 Hz, 1H), 1.70-0.77 (m, 10H). |

Example 21

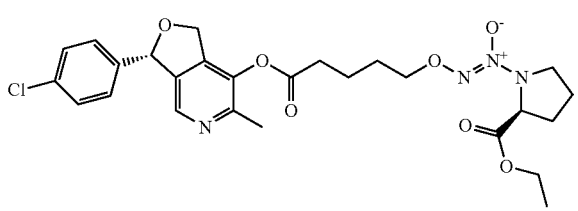 [SMILES: CCOC(=O)[C@@H]1CCCN1/[N+]([O-])=N/OCCCCC(=O)Oc1c(C)ncc2c1CO[C@H]2c1ccc(Cl)cc1]

Ethyl 1-{(Z)-[(5-{[(3S)-3-(4-chlorophenyl)-6-methyl-1,3-dihydrofuro[3,4-c]pyridin-7-yl]oxy}-5-oxopentyl)oxy]-NNO-azoxy}-L-prolinate Step A: tert-butyl 5-bromopentanoate To a solution of 5-bromovaleric acid (1.0 g, 5.52 mmol) in CH$_2$Cl$_2$ (10 mL) at 0° C. was added oxalyl chloride (1.05 g, 8.29 mmol) and followed by a few drops of DMF. After stirring at rt for 2 h, the mixture concentrated and to which tert-butanol (1.64 g, 22.10 mmol) was added. After stirring at rt for 30 min, the mixture was concentrated to afford the title compound.

Step B: tert-butyl 5-({(Z)-2-[(2S)-2-(hydroxymethyl)pyrrolidin-1-yl]-2-oxido-2λ$^5$-diazen-1-yl}oxy)pentanoate To a solution of tert-butyl 5-bromopentanoate (1.20 g, 5.06 mmole) in DMF (15 mL) was added sodium (2S)-2-(hydroxymethyl)-1-[(Z)-oxido-NNO-azoxy]pyrrolidine (1.39 g, 7.59 mmol). The mixture was heated by microwave at 100° C. for 15 min. After cooling down to rt, the mixture was partitioned between Et$_2$O (50 mL) and water (50 mL). The organic layer was washed with brine (3×5 mL), dried over MgSO4, and concentrated. The residue was purified by flash chromatography (Biotage 25+M) using 30-50% EtOAc/hexane gradient, affording the title compound.

Step C: 1-{(Z)-[(5-tert-butoxy-5-oxopentyl)oxy]-NNO-azoxy}-L-proline

To a solution of tert-butyl 5-({(Z)-2-[(2S)-2-(hydroxymethyl)pyrrolidin-1-yl]-2-oxido-2λ$^5$-diazen-1-yl}oxy)pentanoate (440 mg, 1.39 mmol) and sodium periodate (890 mg, 4.16 mmol) in 14 mL of CH$_3$CN/CCl$_4$/H$_2$O (2:2:3) was added ruthenium(III) chloride hydrate (15.6 mg, 0.07 mmol). After stirring at rt over night, the mixture was extracted with CH$_2$Cl$_2$ (3×50 mL), dried over MgSO$_4$ and concentrated to give the title product, which was used directly.

Step D: ethyl 1-{(Z)-[(5-tert-butoxy-5-oxopentyl)oxy]-NNO-azoxy}-L-prolinate To a solution of 1-{(Z)-[(5-tert-butoxy-5-oxopentyl)oxy]-NNO-azoxy}-L-proline (300 mg, 0.91 mmol) in CH$_2$Cl$_2$ (10 mL) was added BOP-Cl (288 mg, 1.13 mmol), followed by triethylamine (137 mg, 1.13 mmol) and ethanol (167 mg, 3.62 mmol). After stirring at rt for 3 h, the mixture was purified by flash chromatography (Biotage 25+M) using 40-60% EtOAc/hexane gradient, affording the title compound.

Step E: 5-({(Z)-2-[(2S)-2-(ethoxycarbonyl)pyrrolidin-1-yl]-2-oxido-2λ$^5$-diazen-1-yl}oxy)pentanoic acid To a solution of ethyl 1-{(Z)-[(5-tert-butoxy-5-oxopentyl)oxy]-NNO-azoxy}-L-prolinate (330 mg, 0.92 mmol) in CH$_2$Cl$_2$ (7 mL) at rt was added trifluoroacetic acid (1.05 g, 9.18 mmol). After stirring at rt over night, the mixture was concentrated to give the title product, which was used directly.

Step F: ethyl 1-{(Z)-[(5-{[(3S)-3-(4-chlorophenyl)-6-methyl-1,3-dihydrofuro[3,4-c]pyridin-7-yl]oxy}-5-oxopentyl)oxy]-NNO-azoxy}-L-prolinate The title compound was made by following the procedures described in EXAMPLE 1 substituting 5-({(Z)-2-[(2S)-2-(ethoxycarbonyl)pyrrolidin-1-yl]-2-oxido-2λ$^5$-diazen-1-yl}oxy)pentanoic acid for 4-[({[(1Z)-2-tert-butyl-2-methyl-1-oxido-1λ$^5$-diazan-1-ylidene]amino}oxy)methyl]benzoic acid in step C. $^1$H NMR (500 MHz, CDCl$_3$) δ 8.06 (s, 1H), 7.37-7.27 (m, 4H), 6.21 (s, 1H), 5.18-5.04 (m, 2H), 4.53 (m, 1H), 4.25 (m, 3H), 3.85 (m, 1H), 3.65 (m, 1H), 2.70 (m, 2H), 2.46 (s, 3H), 2.32 (m, 1H), 2.10 (m, 3H), 1.90 (m, 4H), 1.80 (m, 1H), 1.28 (m, 3H).

Example 22

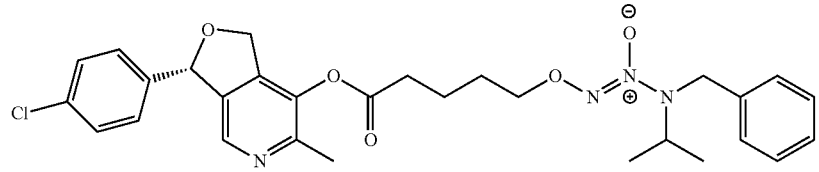 [SMILES: Cc1ncc2c(c1OC(=O)CCCCO/N=[N+](\[O-])N(Cc1ccccc1)C(C)C)CO[C@H]2c1ccc(Cl)cc1]

(3S)-3-(4-Chlorophenyl)-6-methyl-1,3-dihydrofuro[3,4-c]pyridin-7-yl 5-({[(1Z)-2-benzyl-2-isopropyl-1-oxido-1λ$^5$-diazan-1-ylidene]amino}oxy)pentanoate The title compound was made by following the procedures described in EXAMPLE 1 substituting methyl 5-bromovalerate for methyl 4-(bromomethyl)benzoate and sodium (1Z)-3-benzyl-3-isopropyltriaz-1-en-1-olate 2-oxide for sodium (1Z)-3-tert-butyl-3-methyltriaz-1-en-1-olate 2-oxide in step A. $^1$H NMR (500 MHz, CDCl$_3$) δ 8.08 (s, 1H), 7.39-7.27 (m, 9H), 6.22 (s, 1H), 5.16 (dd, J=13.7, 2.4 Hz, 1H), 5.05 (dd, J=13.7, 1.9 Hz, 1H), 4.20 (s, 2H), 4.10 (t, J=6.3 Hz, 2H), 3.68 (septet, J=6.4 Hz, 1H), 2.54 (t, J=7.4 Hz, 2H), 2.46 (s, 3H), 1.71-1.55 (m, 4H), 1.27 (d, J=6.4 Hz, 6H).

Example 23

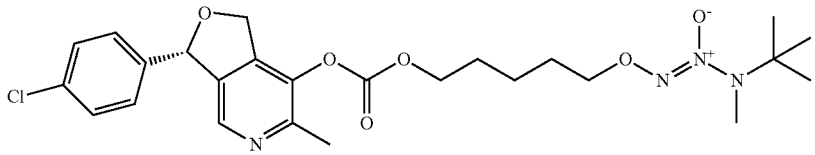

5-({[(1Z)-2-tert-butyl-2-methyl-1-oxido-1λ$^5$-diazan-1-ylidene]amino}oxy)pentyl (3S)-3-(4-chlorophenyl)-6-methyl-1,3-dihydrofuro[3,4-c]pyridin-7-yl carbonate

Step A: 5-({[(1Z)-2-tert-butyl-2-methyl-1-oxido-1λ$^5$-diazan-1-ylidene]amino}oxy)pentyl 1-chloroethyl carbonate To a solution of 5-({[(1Z)-2-tert-butyl-2-methyl-1-oxido-1λ$^5$-diazan-1-ylidene]amino}oxy)-3-methylpentan-1-ol (400 mg, 1.71 mmol) in CH$_2$Cl$_2$ (10 mL) at rt was added 1-chloroethyl chloroformate (294 mg, 2.06 mmol) and followed by pyridine (407 mg, 5.14 mmol). After stirring at rt for 3 h, the mixture was purified by flash chromatography (Biotage 25+M) using 10-30% EtOAc/hexane gradient, affording the title compound: $^1$H NMR (500 MHz, CDCl$_3$) δ 6.30 (m, 1H), 4.16-4.08 (m, 4H), 2.69 (s, 3H), 1.72-1.59 (m, 7H), 1.40 (m, 2H), 1.12 (s, 9H).

Step B: 5-({[(1Z)-2-tert-butyl-2-methyl-1-oxido-1λ$^5$-diazan-1-ylidene]amino}oxy)pentyl (3S)-3-(4-chlorophenyl)-6-methyl-1,3-dihydrofuro[3,4-c]pyridin-7-yl carbonate To a solution of (3S)-3-(4-chlorophenyl)-6-methyl-1,3-dihydrofuro[3,4-c]pyridine-7-ol (270 mg, 1.03 mmol) in DMF (10 mL) at 0° C. was added sodium hydride (61.9 mg, 1.55 mmol) and, in 10 minutes, followed by addition of 5-({[(1Z)-2-tert-butyl-2-methyl-1-oxido-1λ$^5$-diazan-1-ylidene]amino}oxy)pentyl 1-chloroethyl carbonate (425 mg, 1.28 mmol). After stirring at rt for 3 h, the mixture was partitioned between Et$_2$O (50 mL) and water (50 mL). The organic layer was washed with brine (3×50 mL), dried over MgSO4, and concentrated. The residue was purified by flash chromatography (Biotage 25+M) using 30-50% EtOAc/hexane gradient, affording the title compound: $^1$H NMR (500 MHz, CDCl$_3$) δ 8.02 (s, 1H), 7.30-7.22 (m, 4H), 6.15 (s, 1H), 5.22-5.06 (m, 2H), 4.24 (m, 4H), 2.77 (s, 3H), 2.45 (s, 3H), 1.80 (m, 4H), 1.53 (m, 2H), 1.20 (s, 9H).

Example 24

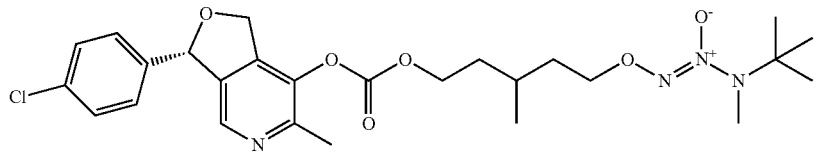 [SMILES: Cc1ncc2c(c1OC(=O)OCCC(C)CCO/N=[N+](\[O-])N(C)C(C)(C)C)CO[C@H]2c1ccc(Cl)cc1]

5-({[(1Z)-2-tert-butyl-2-methyl-1-oxido-1λ$^5$-diazan-1-ylidene]amino}oxy)-3-methylpentyl (3S)-3-(4-chlorophenyl)-6-methyl-1,3-dihydrofuro[3,4-c]pyridin-7-yl carbonate The title compound was made by following the procedures described in EXAMPLE 23 substituting 5-({[(1E)-2-tert-butyl-2-methyl-1-oxidohydrazone]amino}oxy)-3-methylpentan-1-ol (from EXAMPLE 9, Step B) for 5-({[(1Z)-2-tert-butyl-2-methyl-1-oxido-1λ$^5$-diazan-1-ylidene]amino}oxy)-3-methylpentan-1-ol in Step A: $^1$H NMR (500 MHz, CDCl$_3$) δ 8.08 (s, 1H), 7.37-7.27 (m, 4H), 6.21 (s, 1H), 5.27-5.11 (m, 2H), 4.35 (m, 4H), 2.82 (s, 3H), 2.51 (s, 3H), 1.85 (m, 3H), 1.66 (m, 2H), 1.25 (s, 9H), 1.03 (d, J=6.4 Hz, 3H).

Example 25

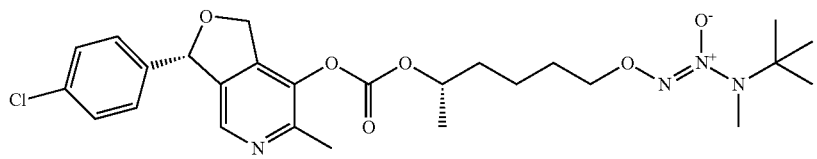 [SMILES: Cc1ncc2c(c1OC(=O)O[C@@H](C)CCCCO/N=[N+](\[O-])N(C)C(C)(C)C)CO[C@H]2c1ccc(Cl)cc1]

(2S)-6-({[(1Z)-2-tert-butyl-2-methyl-1-oxido-1λ$^5$-diazan-1-ylidene]amino}oxy)hexan-2-yl (3 S) 3-(4-chlorophenyl)-6-methyl-1,3-dihydrofuro[3,4-c]pyridin-7-yl carbonate Step A: 6-bromohexan-2-one To a solution of 1-methylcyclopentanol (7.0 g, 69.9 mmol) in CHCl$_3$ (200 mL) at 0° C. was added K$_2$CO$_3$ (58.0 g, 419 mmol) and then carefully Br$_2$ (55.8 g, 349 mmol). The mixture was stirred at 0° C. for 5 h. The reaction was quenched by slowly adding saturated Na$_2$S$_2$O$_3$ (200 mL) and the mixture was extracted with Et$_2$O (200 mL). The organic layer was washed with water (2×200 mL) and brine (3×200 mL), dried over MgSO$_4$, and concentrated to afford the title compound: $^1$H NMR (500 MHz, CDCl$_3$) δ 3.43 (m, 2H), 2.49 (m, 2H), 2.17 (s, 3H), 1.88 (m, 2H), 1.76 (m, 2H).

Step B: 6-({[1Z)-2-tert-butyl-2-methyl-1-oxido-1λ$^5$-diazan-1-ylidene]amino}oxy)hexan-2-one To a solution of 6-bromohexan-2-one (11 g, 61.4 mmole) in DMF (150 mL) was added sodium (1Z)-3-tert-butyl-3-methyltriaz-1-en-1-olate 2-oxide (14 g, 83.0 mmol). The mixture was heated by microwave at 100° C. for 30 min. After cooling down to rt, the mixture was partitioned between Et$_2$O (200 mL) and water (200 mL). The organic layer was separated, washed with brine (3×200 mL), dried over MgSO4, and concentrated. The residue was purified by flash chromatography (Biotage 40+M) using 20-30% EtOAc/hexane gradient, affording the title compound: $^1$H NMR (500 MHz, CDCl$_3$) δ 4.26 (m, 2H), 2.81 (s, 3H), 2.48 (m, 2H), 2.14 (s, 3H), 1.77 (m, 2H), 1.67 (m, 2H), 1.24 (s, 9H).

Step C: (2R)-6-({[(1Z)-2-tert-butyl-2-methyl-1-oxido-1λ$^5$-diazan-1-ylidene]amino}oxy)hexan-2-ol To a 0.5M pH=8.0 phosphate buffer (20 mL, lab prep from K$_2$HPO$_4$, fisher Lot #075904, H$_3$PO$_4$, Fisher Lot #066215 and DI water) in an eppendrof tube was charged with NAD (20 mg, Biocatalysis, Lot #1056121), GDH-103 (20 mg, Biocatalysis, Lot 100705CL) and KRED NAD 101 (20 mg, Bioxcatalysis, Lot #041606WW), and D-glucose (1.656 g). The mixture was transferred to a 50 mL round bottom flask charged with 6-({[(1Z)-2-tert-butyl-2-methyl-1-oxido-1λ$^5$-diazan-1-ylidene]amino}oxy)hexan-2-one (1.5 g) and the resulting mixture was stirred at 30° C. over night. To the reaction mixture was added K$_2$CO$_3$ (8.0 g). After stirring for 15 min, the mixture was extracted with EtOAc (100 mL). The aqueous layer was filtered through a Celite pad and washed with EtOAc (100 mL). The combined organic phase was washed with brine, dried over MgSO$_4$, and concentrated to give an oil: $^1$H NMR (500 MHz, CDCl$_3$) δ 4.28 (m, 2H), 3.80 (m, 1H), 2.82 (s, 31H), 1.80 (m, 2H), 2.50 (m, 5H), 1.25 (s, 9H), 1.20 (d, J=6.2 Hz, 3H).

Step D: (2S)-6-({[(1Z)-2-tert-butyl-2-methyl-1-oxido-1λ$^5$-diazan-1-ylidene]amino}oxy)hexan-2-yl (3S)-3-(4-chlorophenyl)-6-methyl-1,3-dihydrofuro[3,4-c]pyridin-7-yl carbonate The title compound was made by following the procedures described in EXAMPLE 23 substituting (2R)-6-({[(1Z)-2-tert-butyl-2-methyl-1-oxido-1λ$^5$-diazan-1-ylidene]amino}oxy)hexan-2-ol for 5-({[(1Z)-2-tert-butyl-2-methyl-1-oxido-1λ$^5$-diazan-1-ylidene]amino}oxy)-3-methylpentan-1-ol in Step A: $^1$H NMR (500 MHz, CDCl$_3$) δ 8.04 (s, 1H), 7.33-7.24 (m, 4H), 6.17 (s, 1H), 5.24-5.08 (m, 2H), 4.85 (m, 1H), 4.26 (m, 2H), 2.78 (s, 3H), 2.47 (s, 3H), 1.80 (m, 3H), 1.65 (m, 1H), 1.50 (m, 2H), 1.36 (d, J=6.2 Hz, 3H), 1.21 (s, 9H).

Example 26

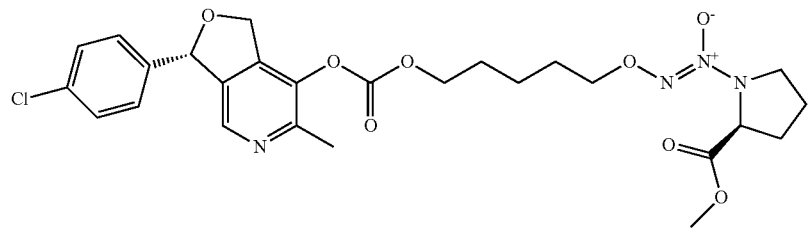 [SMILES: COC(=O)[C@@H]1CCCN1/[N+]([O-])=N/OCCCCCOC(=O)Oc1c(C)ncc2c1CO[C@H]2c1ccc(Cl)cc1]

Methyl 1-[(Z)-({5-[({[(3S)-3-(4-chlorophenyl)-6-methyl-1,3-dihydrofuro[3,4-c]pyridin-7-yl]oxy}carbonyl)oxy]pentyl}oxy)-NNO-azoxy]-L-prolinate

Step A: 5-bromopentyl 4-nitrobenzoate

To a solution of 5-bromo-1-pentanol (8.24 g, 49.3 mmol) in CH₂Cl₂ (40 mL) at 0° C. was added 4-nitrobenzoyl chloride (10.98 g, 59.2 mmol) and followed by pyridine (5.85 g, 74.0 mmol). The mixture was stirred at rt over night and the precipitate was filtered off. The filtrate was purified by flash chromatography (Biotage 65+M) using 20-30% EtOAc/hexane gradient, affording the title compound.

Step B: 5-({(Z)-2-[(2S)-2-(hydroxymethyl)pyrrolidin-1-yl]-2-oxido-2λ⁵-diazen-1-yl}oxy)pentyl 4-nitrobenzoate To a solution of 5-bromopentyl 4-nitrobenzoate (3.0 g, 9.49 mmole) in DMF (40 mL) was added sodium (2S)-2-(hydroxymethyl)-1-[(Z)-oxido-NNO-azoxy]pyrrolidine (2.61 g, 14.2 mmol). The mixture was heated by microwave at 100° C. for 15 min. After cooling to rt, the mixture was partitioned between Et₂O (100 mL) and water (100 mL). The organic layer was separated and washed with brine (3×100 mL), dried over MgSO₄, and concentrated. The residue was purified by flash chromatography (Biotage 25+M) using 30-50% EtOAc/hexane gradient, affording the title compound.

Step C: 1-{(Z)-[(5-{[(4-nitrophenyl)carbonyl]oxy}pentyl)oxy]-NNO-azoxy}-L-proline To a solution of 5-({(Z)-2-[(2S)-2-(hydroxymethyl)pyrrolidin-1-yl]-2-oxido-2λ⁵-diazen-1-yl}oxy)pentyl 4-nitrobenzoate (1.0 g, 2.52 mmol) and sodium periodate (1.62 g, 7.57 mmol) in 14 mL of CH₃CN/CCl₄/H₂O (2:2:3) was added ruthenium(III) chloride hydrate (57 mg, 0.25 mmol). After stirring at rt over night, the mixture was extracted with CH₂Cl₂ (3×50 mL), dried over MgSO₄, and concentrated to give the title product, which was used directly.

Step D: methyl 1-{(Z)-[(5-{[(4-nitrophenyl)carbonyl]oxy}pentyl)oxy]-NNO-azoxy}-L-prolinate To a solution of 1-{(Z)-[(5-{[(4-nitrophenyl)carbonyl]oxy}pentyl)oxy]-NNO-azoxy}-L-proline (880 mg, 2.14 mmol) in CH₂Cl₂ (10 mL) was added BOP-Cl (682 mg, 2.68 mmol), followed by triethylamine (325 mg, 3.22 mmol) and methanol (275 mg, 8.58 mmol). After stirring at rt for 3 h, the mixture was purified by flash chromatography (Biotage 25+M) using 40-60% EtOAc/hexane gradient, affording the title compound.

Step E: methyl 1-{(Z)-[(5-hydroxypentyl)oxy]-NNO-azoxy}-L-prolinate

To a solution of methyl 1-{(Z)-[(5-{[(4-nitrophenyl)carbonyl]oxy}pentyl)oxy]-NNO-azoxy}-L-prolinate (420 mg, 0.98 mmol) in methanol (8 mL) at rt was added potassium carbonate (203 mg, 1.47 mmol). After stirring at rt for 15 min, the solid was filtered off. The filtrate was purified by flash chromatography (Biotage 25+M) using 30-70% EtOAc/hexane gradient, affording the title compound.

Step F: methyl 1-[(Z)-({5-[({[(3S)-3-(4-chlorophenyl)-6-methyl-1,3-dihydrofuro[(3,4-c]pyridin-7-yl]oxy}carbonyl)oxy]pentyl}oxy)-NNO-azoxy]-L-prolinate The title compound was made by following the procedures described in EXAMPLE 23 substituting methyl 1-{(Z)[(5-hydroxypentyl)oxy]-NNO-azoxy}-L-prolinate for 5-({[(1Z)-2-tert-butyl-2-methyl-1-oxido-1λ⁵-diazan-1-ylidene]amino}oxy)-3-methylpentan-1-ol in Step A: ¹H NMR (500 MHz, CDCl₃) δ 8.06 (s, 1H), 7.35-7.26 (m, 4H), 6.19 (s, 1H), 5.25-5.09 (m, 2H), 4.65 (m, 1H), 4.30 (m, 2H), 4.20 (m, 2H), 3.83 (m, 1H), 3.74 (s, 3H), 3.63 (m, 1H), 2.49 (s, 3H), 2.30 (m, 1H), 2.05 (m, 3H), 1.80 (m, 4H), 2.56 (m, 2H).

Compounds of the invention were evaluated for blood pressure reduction efficacy using the following canine telemetry protocol.

Male beagle dogs (approximately 1-3 years old) with a body weight of between 10 and 16 kg were surgically implanted with DSI radiotelemetry devices (model: TL11M2-D70-PCT). Briefly, under an inhalant anesthesia, isoflurane/oxygen mixture (1-3.5%/to effect), the body of the telemetry device was positioned and secured intra-abdominally. Subsequently, the arterial catheter of the telemetry device was passed subcutaneously to the inguinal area and introduced into the femoral artery and advanced to the level of the descending aorta. The catheter was secured with 2-0 silk ligatures. The muscle and underlying fascia was closed over the catheter using absorbable suture and the skin was closed using non-absorbable suture. The animals were allowed a minimum recovery period of 2 weeks between surgery and the evaluation of test compounds.

Compound evaluation consisted of a 3 day paradigm at a 3 mg/kg dose. On the first day, no compounds were administered during a 24 hour period of baseline data collection. Blood pressure and heart rate data were collected continuously for one minute periods at 10 minute intervals. On the days of compound administration half the animals received test article with the other half receiving the vehicle used for compound formulation. All test materials were administered by oral gavage in a volume of 1 mL/kg. Data are expressed either as raw values (mm Hg or beats per minute) or as the change from baseline (average value for about 12 hours in low activity period prior to dosing). Change is SBP (systolic blood pressure) and PP (pulse pressure) over time is shown below:

| Compound | ΔSBP (mm Hg) | | | ΔPP (mm Hg) | | |
|---|---|---|---|---|---|---|
| | 1-6 h | 6-12 h | 12-18 h | 1-6 h | 6-12 h | 12-18 h |
| 8 | −15 | −12 | −2 | −12 | −8 | −4 |
| 13 | −30 | −15 | −4 | −22 | −11 | −6 |
| 14 | −21 | −8 | 3 | −18 | −9 | −3 |
| 6 | −16 | −6 | −1 | −16 | −7 | −3 |
| 5 | −11 | −2 | 2 | −10 | −3 | 1 |
| 25 | −14 | −7 | 0 | −12 | −7 | −4 |

What is claimed is:
1. A compound of the formula I:

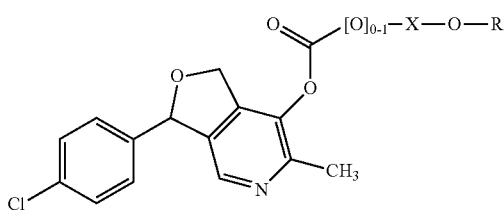

or a pharmaceutically acceptable salt thereof, wherein R is selected from the group consisting of

1)

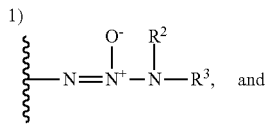

2)

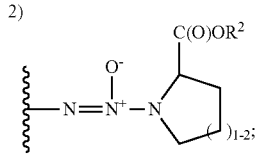

$R^2$, in each instance in which it occurs, is independently —$C_{1-6}$alkyl;
$R^3$ is —$C_{1-6}$alkyl or —$C_{1-6}$alkylene-aryl;
X is selected from the group consisting of

1)

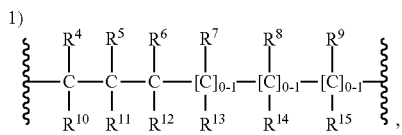

2)

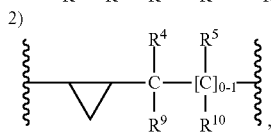

3)

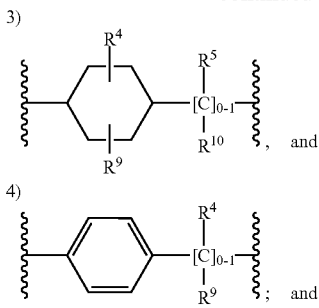

4)

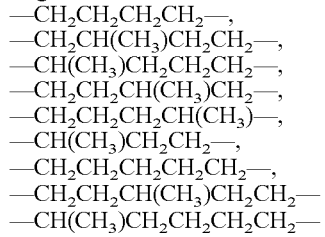

$R^4$, $R^5$, $R^6$, $R^7$, $R^8$, $R^9$, $R^{10}$, $R^{11}$, $R^{12}$, $R^{13}$, $R^{14}$ and $R^{15}$ are independently selected from the group consisting of hydrogen, $C_{1-6}$ alkyl, halogen, and —O—$C_{1-6}$ alkyl.

2. A compound of claim 1, or a pharmaceutically acceptable salt thereof, wherein X is selected from the group consisting of
—CH$_2$CH$_2$CH$_2$CH$_2$—,
—CH$_2$CH(CH$_3$)CH$_2$CH$_2$—,
—CH(CH$_3$)CH$_2$CH$_2$CH$_2$—,
—CH$_2$CH$_2$CH(CH$_3$)CH$_2$—,
—CH$_2$CH$_2$CH$_2$CH(CH$_3$)—,
—CH(CH$_3$)CH$_2$CH$_2$—,
—CH$_2$CH$_2$CH$_2$CH$_2$CH$_2$—,
—CH$_2$CH$_2$CH(CH$_3$)CH$_2$CH$_2$—
—CH(CH$_3$)CH$_2$CH$_2$CH$_2$CH$_2$—

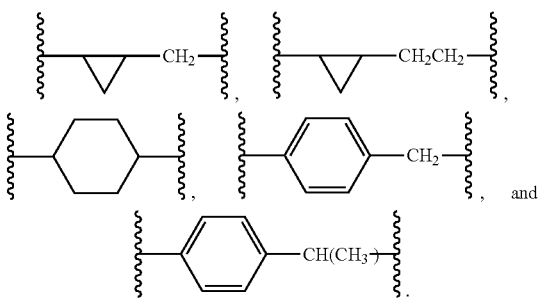

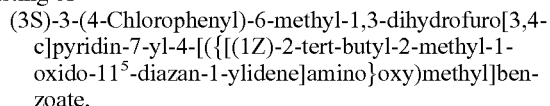

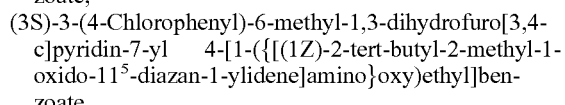

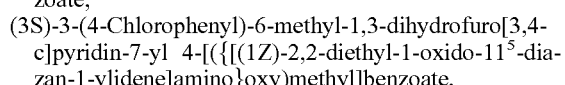

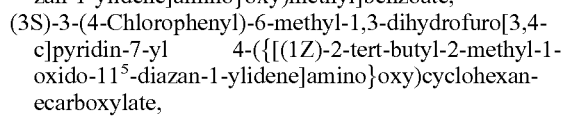

3. A compound of claim 1, or a pharmaceutically acceptable salt thereof, wherein $R^2$ is selected from the group consisting of —CH$_3$, —CH$_2$CH$_3$, —C(CH$_3$)$_3$, and —CH(CH$_3$)$_2$.

4. A compound of claim 1, or a pharmaceutically acceptable salt thereof, wherein $R^3$ is selected from the group consisting of —CH$_3$, —CH$_2$CH$_3$, —C(CH$_3$)$_3$, —CH(CH$_3$)$_2$ and —CH$_2$—C$_6$H$_5$.

5. A compound of claim 1, selected from the group consisting of
(3S)-3-(4-Chlorophenyl)-6-methyl-1,3-dihydrofuro[3,4-c]pyridin-7-yl-4-[({[(1Z)-2-tert-butyl-2-methyl-1-oxido-11$^5$-diazan-1-ylidene]amino}oxy)methyl]benzoate,
(3S)-3-(4-Chlorophenyl)-6-methyl-1,3-dihydrofuro[3,4-c]pyridin-7-yl 4-[1-({[(1Z)-2-tert-butyl-2-methyl-1-oxido-11$^5$-diazan-1-ylidene]amino}oxy)ethyl]benzoate,
(3S)-3-(4-Chlorophenyl)-6-methyl-1,3-dihydrofuro[3,4-c]pyridin-7-yl 4-[({[(1Z)-2,2-diethyl-1-oxido-11$^5$-diazan-1-ylidene]amino}oxy)methyl]benzoate,
(3S)-3-(4-Chlorophenyl)-6-methyl-1,3-dihydrofuro[3,4-c]pyridin-7-yl 4-({[(1Z)-2-tert-butyl-2-methyl-1-oxido-11$^5$-diazan-1-ylidene]amino}oxy)cyclohexanecarboxylate, (3S)-3-(4-Chlorophenyl)-6-methyl-1,3-dihydrofuro[3,4-c]pyridin-7-yl cis-4-({[(1Z)-2-tert-butyl-2-methyl-1-oxidohydrazono]amino}oxy)cyclohexanecarboxylate, (3S)-3-(4-Chlorophenyl)-6-methyl-1,3-dihydrofuro[3,4-c]pyridin-7-yl trans-4-({[(1Z)-2-tert-butyl-2-methyl-1-oxidohydrazono]amino}oxy)cyclohexanecarboxylate, (3S)-3-(4-Chlorophenyl)-6-methyl-1,3-dihydrofuro[3,4-c]pyridin-7-yl trans-4-({[(1Z)-2,2-diethyl-1-oxido-11$^5$-diazan-1-ylidene]amino}oxy)cyclohexanecarboxylate, (3S)-3-(4-Chlorophenyl)-6-methyl-1,3-dihydrofuro[3,4-c]pyridin-7-yl 5-({[(1Z)-2-tert-butyl-2-methyl-1-oxido-11$^5$-diazan-1-ylidene]amino}oxy)pentanoate, (3S)-3-(4-Chlorophenyl)-6-methyl-1,3-dihydrofuro[3,4-c]pyridin-7-yl 5-({[(1Z)-2-tert-butyl-2-methyl-1-oxido-11$^5$-diazan-1-ylidene]amino}oxy)-3-methylpentanoate, (3S)-3-(4-Chlorophenyl)-6-methyl-1,3-dihydrofuro[3,4-c]pyridin-7-yl (3R)-5-({[(1Z)-2-tert-butyl-2-methyl-1-oxido-11$^5$-diazan-1-ylidene]amino}oxy)-3-methylpentanoate, (3S)-3-(4-Chlorophenyl)-6-methyl-1,3-dihydrofuro[3,4-c]pyridin-7-yl (3S)-5-({[(1Z)-2-tert-butyl-2-methyl-1-oxido-11$^5$-diazan-1-ylidene]amino}oxy)-3-methylpentanoate, (3S)-3-(4-Chlorophenyl)-6-methyl-1,3-dihydrofuro[3,4-c]pyridin-7-yl 5-({[(1Z)-2-tert-butyl-2-methyl-1-oxido-11$^5$-diazan-1-ylidene]amino}oxy)-2-methylpentanoate, (3S)-3-(4-Chlorophenyl)-6-methyl-1,3-dihydrofuro[3,4-c]pyridin-7-yl 5-({[(1Z)-2-tert-butyl-2-methyl-1-oxido-11$^5$-diazan-1-ylidene]amino}oxy)-4-methylpentanoate, (3S)-3-(4-Chlorophenyl)-6-methyl-1,3-dihydrofuro[3,4-c]pyridin-7-yl 5-({[(1Z)-2-tert-butyl-2-methyl-1-oxido-11$^5$-diazan-1-ylidene]amino}oxy)hexanoate, (3S)-3-(4-Chlorophenyl)-6-methyl-1,3-dihydrofuro[3,4-c]pyridin-7-yl 4-({[(1E)-2-tert-butyl-2-methyl-1-oxidohydrazono]amino}oxy)-2-methylbutanoate, (3S)-3-(4-Chlorophenyl)-6-methyl-1,3-dihydrofuro[3,4-c]pyridin-7-yl 2-[2-({[(1Z)-2-tert-butyl-2-methyl-1-oxidohydrazono]amino}oxy)ethyl]-trans-cyclopropanecarboxylate, (3S)-3-(4-Chlorophenyl)-6-methyl-1,3-dihydrofuro[3,4-c]pyridin-7-yl 2-[2-({[(1Z)-2-tert-butyl-2-methyl-1-oxidohydrazono]amino}oxy)ethyl]-cis-cyclopropanecarboxylate, (3S)-3-(4-Chlorophenyl)-6-methyl-1,3-dihydrofuro[3,4-c]pyridin-7-yl 2-[({[2-tert-butyl-2-methyl-1-oxido-11$^5$-diazan-1-ylidene]amino}oxy)methyl]cyclopropanecarboxylate, Ethyl 1-{(Z)-[(5-{[(3S)-3-(4-chlorophenyl)-6-methyl-1,3-dihydrofuro[3,4-c]pyridin-7-yl]oxy}-5-oxopentyl)oxy]-NNO-azoxy}-L-prolinate, (3S)-3-(4-Chlorophenyl)-6-methyl-1,3-dihydrofuro[3,4-c]pyridin-7-yl 5-({[(1Z)-2-benzyl-2-isopropyl-1-oxido-11$^5$-diazan-1-ylidene]amino}oxy)pentanoate, 5-({[(1Z)-2-tert-butyl-2-methyl-1-oxido-11$^5$-diazan-1-ylidene]amino}oxy)pentyl (3S)-3-(4-chlorophenyl)-6-methyl-1,3-dihydrofuro[3,4-c]pyridin-7-yl carbonate, 5-({[(1Z)-2-tert-butyl-2-methyl-1-oxido-11$^5$-diazan-1-ylidene]amino}oxy)-3-methylpentyl (3S)-3-(4-chlorophenyl)-6-methyl-1,3-dihydrofuro[3,4-c]pyridin-7-yl carbonate, (2S)-6-({[(1Z)-2-tert-butyl-2-methyl-1-oxido-11$^5$-diazan-1-ylidene]amino}oxy)hexan-2-yl (3S)-3-(4-chlorophenyl)-6-methyl-1,3-dihydrofuro[3,4-c]pyridin-7-yl carbonate, and Methyl 1-[(Z)-({5-[({[(3S)-3-(4-chlorophenyl)-6-methyl-1,3-dihydrofuro[3,4-c]pyridin-7-yl]oxy}carbonyl)oxy]pentyl}oxy)-NNO-azoxy]-L-prolinate, or a pharmaceutically acceptable salt thereof.

6. A pharmaceutical composition comprising a compound of claim 1 and a pharmaceutically acceptable carrier.

7. A pharmaceutical composition comprising a compound of claim 5 and a pharmaceutically acceptable carrier.

8. A pharmaceutical composition comprising a compound of claim 1, a diuretic, and a pharmaceutically acceptable carrier.

9. A method for treating hypertension in a patient which comprises administering to the patient a therapeutically effective amount of the composition of claim 6.

* * * * *